United States Patent
McNair

(10) Patent No.: US 10,566,082 B1
(45) Date of Patent: *Feb. 18, 2020

(54) PROXIMITY-BASED MOBILE-DEVICE UPDATES OF ELECTRONIC HEALTH RECORDS

(71) Applicant: CERNER INNOVATION, INC., Kansas City, KS (US)

(72) Inventor: Douglas S. McNair, Leawood, KS (US)

(73) Assignee: CERNER INNOVATION, INC., Kansas City, KS (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/997,469

(22) Filed: Jun. 4, 2018

Related U.S. Application Data

(63) Continuation-in-part of application No. 15/395,330, filed on Dec. 30, 2016, which is a continuation of
(Continued)

(51) Int. Cl.
  *G16H 10/60* (2018.01)
  *G16H 10/65* (2018.01)
  (Continued)

(52) U.S. Cl.
  CPC ............. *G16H 10/65* (2018.01); *G06F 16/90* (2019.01); *G06F 16/955* (2019.01); *G06F 19/00* (2013.01);
  (Continued)

(58) Field of Classification Search
  CPC ........ G16H 10/20; G16H 10/60; G06K 19/00; G06K 7/10861; G06Q 10/87
  (Continued)

(56) References Cited

U.S. PATENT DOCUMENTS 6,047,257 A    4/2000  Dewaele
7,546,954 B2   6/2009  Longacre, Jr. et al.
(Continued)

OTHER PUBLICATIONS

First Action Interview Office Action received for U.S. Appl. No. 15/395,330 dated Dec. 18, 2017, 5 pages.
(Continued)

*Primary Examiner* — Edwyn Labaze
(74) *Attorney, Agent, or Firm* — Shook, Hardy & Bacon L.L.P.

(57) ABSTRACT

A system, method, and computer-readable media are provided for facilitating clinical decision making, and in particular, decision making based on a third party's clinical situation by determining and providing useful, up-to-date information, such as patient-related information to a decision maker. In one embodiment, a user first identifies an information item concerning a patient. Based on that item, a set of related information items is determined and prioritized, and a reference pointer, which identifies the set of related information, is generated. The reference pointer is communicated to the user's mobile device. Subsequently, the user's mobile device requests information from the set of information items associated with the reference pointer, and provides information authorization information. Following authentication of the user's credentials, updates of information from the set of information items may be communicated to the user's mobile device as they become available.

20 Claims, 13 Drawing Sheets

Related U.S. Application Data application No. 14/841,093, filed on Aug. 31, 2015, now Pat. No. 9,633,169, which is a continuation of application No. 13/738,277, filed on Jan. 10, 2013, now Pat. No. 9,141,726.

(60) Provisional application No. 62/514,784, filed on Jun. 3, 2017, provisional application No. 61/585,102, filed on Jan. 10, 2012.

(51) Int. Cl.
| | | |
|---|---|---|
| *G06F 19/00* | (2018.01) | |
| *G16H 40/63* | (2018.01) | |
| *G06F 21/62* | (2013.01) | |
| *G06Q 50/22* | (2018.01) | |
| *G06F 16/90* | (2019.01) | |
| *G06F 16/955* | (2019.01) | |

(52) U.S. Cl.
CPC ......... *G06F 21/6245* (2013.01); *G06Q 50/22* (2013.01); *G16H 10/60* (2018.01); *G16H 40/63* (2018.01)

(58) Field of Classification Search
USPC .................. 235/375, 487, 475; 705/11–25
See application file for complete search history.

(56) References Cited

U.S. PATENT DOCUMENTS

| | | | |
|---|---|---|---|
| 7,698,269 | B2 | 4/2010 | Zhou et al. |
| 7,698,347 | B2 | 4/2010 | Vidya Sagar |
| 7,992,773 | B1 | 8/2011 | Rothschild |
| 8,054,177 | B2 | 11/2011 | Graves et al. |
| 9,633,169 | B1 | 4/2017 | McNair |
| 2001/0049274 | A1 | 12/2001 | Degraeve |
| 2002/0111830 | A1 | 8/2002 | Tahan |
| 2002/0152239 | A1 | 10/2002 | Bautista-Lloyd et al. |
| 2003/0074328 | A1 | 4/2003 | Schiff et al. |
| 2003/0182414 | A1 | 9/2003 | O'Neill |
| 2004/0153344 | A1 | 8/2004 | Bui et al. |
| 2006/0229918 | A1 | 10/2006 | Fotsch et al. |
| 2006/0255143 | A1 | 11/2006 | Ehrhart |
| 2007/0043879 | A1 | 2/2007 | Vidya Sagar |
| 2007/0083535 | A1 | 4/2007 | Zilliacus et al. |
| 2007/0136202 | A1 | 6/2007 | Noma et al. |
| 2007/0136279 | A1 | 6/2007 | Zhou et al. |
| 2007/0138253 | A1 | 6/2007 | Libin et al. |
| 2007/0282633 | A1 | 12/2007 | Haider et al. |
| 2008/0021834 | A1 | 1/2008 | Holla et al. |
| 2008/0126729 | A1 | 5/2008 | Cai et al. |
| 2008/0208897 | A1 | 8/2008 | Lew et al. |
| 2009/0037224 | A1 | 2/2009 | Raduchel |
| 2009/0069000 | A1 | 3/2009 | Kindberg et al. |
| 2009/0222353 | A1 | 9/2009 | Guest et al. |
| 2010/0042824 | A1 | 2/2010 | Lee et al. |
| 2010/0280847 | A1 * | 11/2010 | Schaffer ................ G16H 50/20 705/3 |
| 2011/0112850 | A1 | 5/2011 | Beraja et al. |
| 2011/0276349 | A1 | 11/2011 | Huang et al. |
| 2011/0295078 | A1 | 12/2011 | Reid et al. |
| 2012/0041774 | A1 | 2/2012 | Schmitt et al. |
| 2012/0295078 | A1 | 11/2012 | Kondo et al. |

OTHER PUBLICATIONS

Notice of Allowance received for U.S. Appl. No. 13/738,277 dated May 18, 2015, 10 pages.

Non-Final Office Action dated Jul. 9, 2018 in U.S. Appl. No. 15/395,330, 18 pages.

Non-Final Office Action received for U.S. Appl. No. 15/395,330, dated Nov. 28, 2018, 15 pages.

* cited by examiner

PATIENT: DOE, JANE MARY
AGE: 62

CURRENT CONDITIONS
- ☒ HYPERTENSION, BPG2
- ☐ ARTIRIAL FIBRILLATION
- ☒ HYPERGLYCEMIA

CURRENT LEVELS
| | |
|---|---|
| BP | 155/95 MG |
| ATRIAL | 188 |
| BLOOD GLUCOSE | 400 MG/DL |
| SODIUM | 130 MGQ/L |
| POTASSIUM | 3.4 MEQ/L |
| HBA1C | 8.5 % |
| WEIGHT | 95 KG |
| BMI | 30 KG/M2 |
| WAIST/HIP RATIO | 0.98 |

*FIG. 4A.*

PATIENT: DOE, JANE MARY
AGE: 62

CURRENT CONDITIONS
- ☒ HYPERTENSION, BPG2
- ☐ ARTIRIAL FIBRILLATION
- ☒ HYPERGLYCEMIA

CURRENT LEVELS — 142
| | |
|---|---|
| BP | 155/95 MG |
| ATRIAL | 188 |
| BLOOD GLUCOSE | 400 MG/DL |
| SODIUM | 130 MEQ/L |
| POTASSIUM | 3.4 MEQ/L |
| HBA1C | 8.5 % |
| WEIGHT | 95 KG |
| BMI | 30 KG/M2 |
| WAIST/HIP RATIO | 0.98 |

*FIG. 4B.*

PROXIMITY-BASED MOBILE-DEVICE UPDATES OF ELECTRONIC HEALTH RECORDS

CROSS-REFERENCE TO RELATED APPLICATIONS

This application claims the benefit of U.S. Provisional Application No. 62/514,784, filed Jun. 3, 2017, entitled "PROXIMITY-BASED MOBILE-DEVICE UPDATES OF ELECTRONIC HEALTH RECORDS." This application is a continuation-in-part of co-pending U.S. patent application Ser. No. 15/395,330, filed on Dec. 30, 2016, entitled "COMPUTERIZED SYSTEMS AND METHODS FOR PROVIDING MOBILE-DEVICE UPDATES OF ELECTRONIC HEALTH RECORDS," which is a continuation of U.S. patent application Ser. No. 14/841,093, filed Aug. 31, 2015, which, itself, is a continuation of U.S. patent application Ser. No. 13/738,277, filed Jan. 10, 2013, which claims the benefit of U.S. Provisional Application No. 61/585,102, filed Jan. 10, 2012. Each of the aforementioned applications is assigned or under obligation of assignment to the same entity as this application, and incorporated in this application by reference in their entireties.

BACKGROUND

The modern practice of medicine poses a number of information-related challenges for clinicians to effectively deliver quality care to patients. Likewise, information-related challenges arise for patients and their family members, challenges to their effectively tracking and responding to new information that arises at various times during the processes of preventive interventions and care delivery. In particular, the rate of ongoing arrival of new information about each patient's health continues to grow at a rapid pace, making it difficult for clinicians to keep up with and carry out recognized best practices in a timely, responsive manner. The difficulty for patients or for family member caregivers to keep apprised of new information concerning their own health conditions or those of the family members for whose care they are responsible is exacerbated by the fact that consumers are typically pulled in many different directions by a vast number of daily concerns.

In a similar manner, clinicians have their attention fragmented by heavy patient loads and must often make quick decisions regarding a patient's treatment. The limited time available when new information materializes may be too short to permit the clinician or the consumer to consult the entirety of the individual's electronic health record or personal health record, 'pull' a collection of older context-providing information, and acquaint or reacquaint himself/herself with the context into which the new information fits. As a result, gaps currently exist between recognized best practices and actual clinician decisions; gaps also exist between optimal, fully-deliberated consumer intentions and actual consumer decisions. These gaps contribute to delays, decreased quality of care, increased risk of medical errors, and increased cost of health care.

SUMMARY

Systems, methods, and computer-readable media are provided for facilitating clinical decision making based on a patient's clinical situation by providing up-to-date information, such as patient-related information, to a decision maker. In one embodiment, the method includes the step of receiving a selection of one or more information items associated with a third person. For example, a healthcare provider might select a particular topic, concept, or group of interrelated concepts, such as heart-related data, associated with a third-person patient. The method also includes the steps of determining a set of information items related to the one or more selected items. The method also includes the step of associating with the set of information items, a reference pointer, which identifies the set of information items and in some embodiments encodes the reference pointer in a wireless-communications (such as Bluetooth Low Energy or BLE, or Bluetooth 4.0) beacon or transponder configured as a fob, tag, card, or, in some embodiments, as a subsystem within another device, such as a smartwatch, fitness tracker band, or mobile phone or tablet computer. The method further includes communicating the reference pointer to a user device, and receiving from the user device a request for information from the set of information identified by the reference pointer. The method further includes the step of providing a subset of information items in the set to the user device.

In an embodiment, the subset of information items provided to the user device is based upon a set of criteria that can include, for example, the staleness of the information items and the relevance of the information items to a patient's condition. In an embodiment, the credentials are also received from the user device, which indicate which information items a user, associated with the user device, is permitted to access or how long a portion of the information items should remain accessible to the user device.

BRIEF DESCRIPTION OF THE DRAWINGS

The present invention is described in detail below with reference to the attached drawing figures, wherein:

FIGS. 4A, 4B, and 4C depict examples of user interfaces suitable for use in embodiments of the disclosure;

DETAILED DESCRIPTION

Figure 1A:
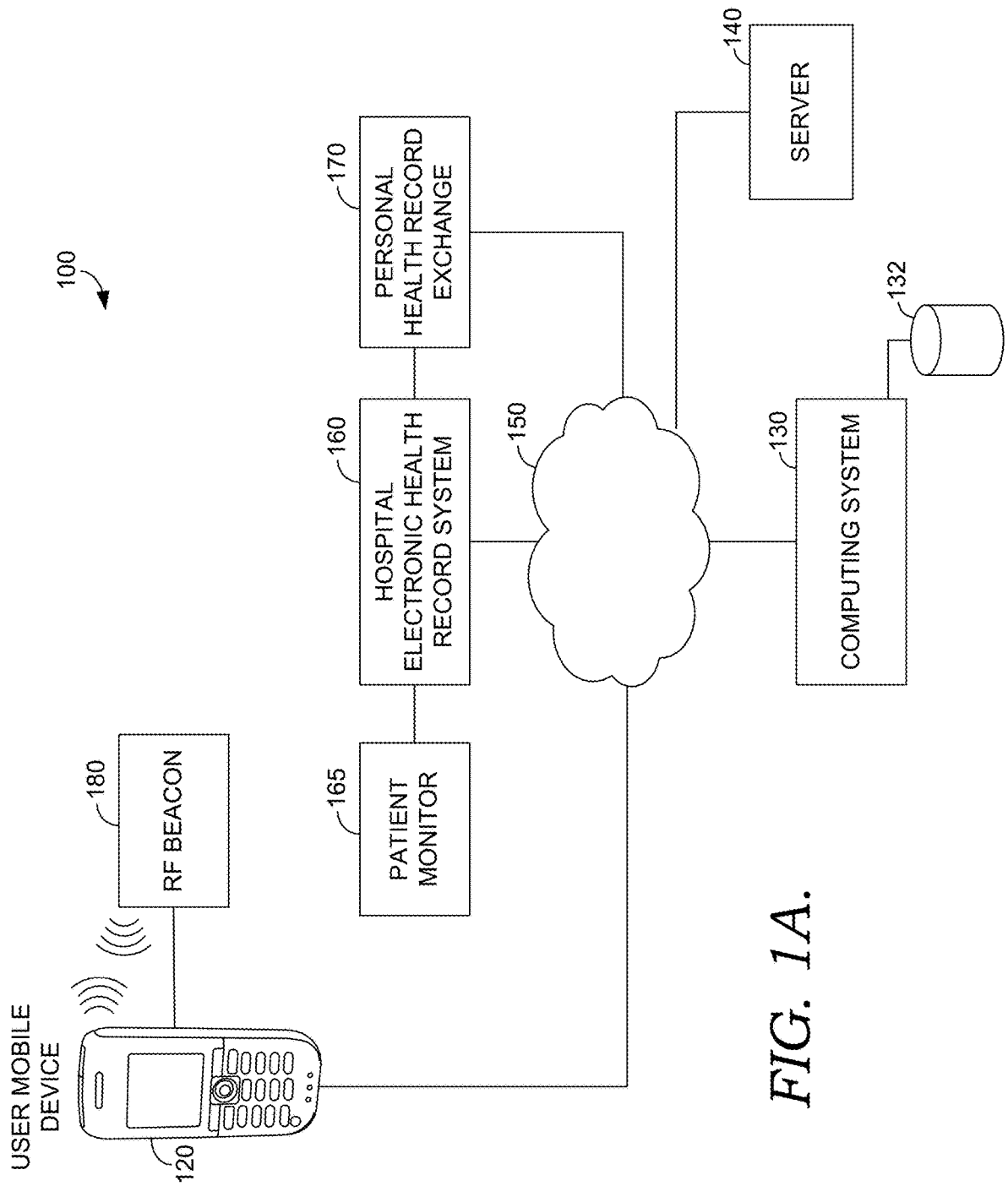
FIGS. 1A, 1B, 1C, and 1D depict embodiments of the invention and aspects of an illustrative operating environment suitable for practicing embodiments of the present disclosure.

The subject matter of the present disclosure is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

As one skilled in the art will appreciate, embodiments of this disclosure may be embodied as, among other things: a method, system, or set of instructions embodied on one or more computer readable media. Accordingly, the embodiments may take the form of a hardware embodiment, a software embodiment, or an embodiment combining software and hardware. In one embodiment, the present technology takes the form of a computer-program product that includes computer-usable instructions embodied on one or more computer readable media.

Computer-readable media can be any available media that can be accessed by a computing device and includes both volatile and nonvolatile media, removable and non-removable media. By way of example, and not limitation, computer-readable media comprises media implemented in any method or technology for storing information, including computer-storage media and communications media. Computer storage media includes both volatile and nonvolatile, removable and non-removable media implemented in any method or non-transitory technology for storage of information such as computer-readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by computing device. Computer storage media does not comprise signals per se. Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer-readable media.

A convenient means to request to receive updated information such as patient-oriented, venue-oriented, or role-oriented topics of ongoing relevance to the clinician requestor or consumer requestor is provided, using for example mobile devices. Tagging and requesting topical, concept-oriented clusters of information so as to cause automatic 'push' or 'pull' delivery of the means to retrieve concise, context-associated information clusters via mobile phones or other media utilized by the requestor can effectively ameliorate cognitive gaps and solve the problems discussed above. The meaning of the new information pertaining to the patient is thus more readily apprehended, and this can in turn promote better, more timely healthcare decisions.

Figures 6A, 6B, 6C:
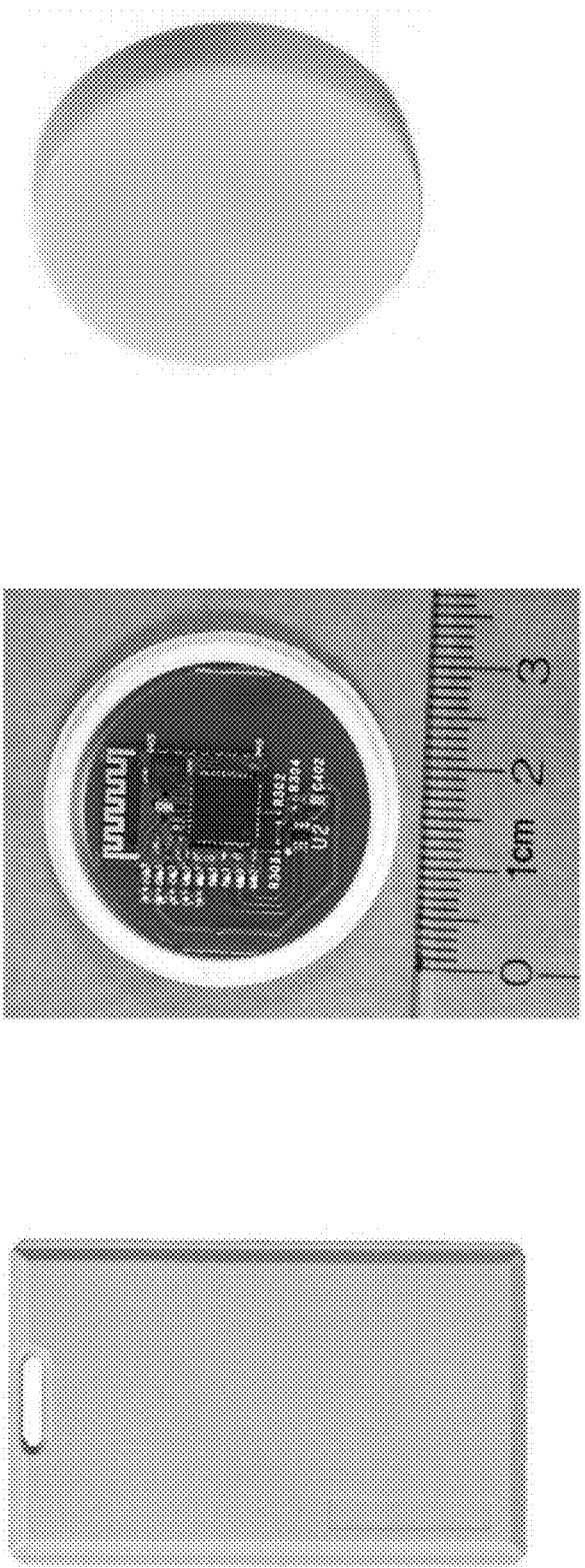
FIGS. 6A-6C depict example RF (BLE-type) beacons suitable for use in embodiments of this disclosure.

Embodiments of the present invention provide a computerized system, methods, and computer-readable media for use in facilitating clinical decision making based on a patient's clinical situation. By way of example and not limitation, in an example embodiment, the entry of a wireless-communications-beacon-bearing patient into spatial proximity to an authorized user possessing a Bluetooth Low Energy (BLE)-enabled mobile device is detected on a software application (e.g., an app) running on the user's mobile device, such as application 143 described in connection to FIG. 1B. The beacon may be an RF BLE-type beacon, for example, such as shown in FIGS. 6A-6C, and be associated with a particular patient. The beacon may broadcast or "advertise" an indication of the patient, such as a reference pointer corresponding to the patient's EHR information (or subset of patient EHR information) such that the indication is detected by the mobile device upon entry into the spatial proximity of the beacon. In this way, some embodiments provide or enable a context-aware provisioning of health information and health-related decision-support communications to a nearby human clinician or other caregiver, via a BLE-enabled mobile device.

In one embodiment, the beacon may be a tag or token that is carried by the patient, in a purse or wallet, for example. In another embodiment, the beacon may be a tag that is worn by the patient but in a location that may not be in close proximity to nor in direct contact with flesh, such as in a clothing pocket, for example. In yet another embodiment, the beacon may be a wearable device that is affixed to flesh or in close proximity to or in contact with bare skin, such as a band or bracelet, which is worn more or less continuously by the user.

The software app may automatically activate upon receiving the indication or reference pointer beacon, or may be set to a listening mode by the user. The app may respond, either automatically or by manual action by the user, to the BLE beacon advertisement. If the user is a clinician who is responsible for the care of, or a portion of the care of, the patient and has previously been so authorized, then the app may respond by binding to (or otherwise associating) the beacon and retrieving updated clinical and EHR or PHR information, from the EHR and/or PHR systems and, optionally, from the BLE beacon itself. Similarly, if the user is a family member or other authorized caregiver of the patient, then the app may likewise respond by binding to or associating the beacon and retrieving updated information pertaining to the patient.

In one embodiment, a transaction that establishes binding or association of the user's mobile device app to the patient's BLE beacon may soon thereafter trigger an online request to subscribe to a particular topic, concept, or set of interrelated concepts associated with a third party such as a patient, venue, or role by interrogating current problem list items or diagnoses, current ordered treatments or procedures, current medication list items, current associated health insurers or health plan indicia, current associated providers or pharmacies serving the BLE beacon-bearing patient, or otherwise selecting (i.e., tagging) one or more items of interest pertaining to the ongoing care of said patient. A health information system responds by dynamically retrieving a set of information associated with the combination of concepts that are associated with the indicated items. The set of associated information (or a portion of it, based on relevance or other criteria as described herein) may be made available on the mobile device for subsequent review or action. In an embodiment, the set of associated information (or the portion of it described herein), may be displayed on the user interface of the mobile device; for example, the set of associated information may be displayed while the EHR of the patient is in an unopened state, permitting the user the summarized information to be presented to the user without the mobile device expending resources to open the EHR application and/or the EHR itself. In some embodiments, the user's identity is authenticated by the information system and the user's access privileges are checked.

In some embodiments, the subscription duration is based on the spatial proximity to the beacon. For example, in one embodiment when the user's mobile device is no longer within range of the beacon, the app may no longer receive information about the patient. In some embodiments, spatial proximity is a factor in determining relevance when the system determines what subscribed-to information should be communicated to and/or displayed on the mobile device. Thus, where a user has "subscribed" (such as discussed above) to information about multiple patients (or multiple targets associated with beacons), the subscribed-to information may be ranked, prioritized, and/or analyzed for relevance based in part on proximity. For example, the subscribed-to information from patients not in proximity may not be provided (or not be presented on the user device) or this information may be presented below or after other subscribed-to information about patients who are in spatial proximity to the mobile device. In other words, for patient information (or targets) that a caregiver subscribes to, information about patients who are not present may not be presented to the user or may be presented after the information about patients who are present. In some embodiments, a user may selectively determine which subscriptions to keep or provide regardless of proximity, and which to de-subscribe-to or not display, based in part on proximity. Thus it is contemplated that a user (or system administrator) may adjust the weighting of spatial proximity as a factor in determining relevance of the information displayed to the end user. For example, it is contemplated that in some instances critical information about a patient not present may be determined more relevant than certain information about present patients, and thus the critical information may be prioritized and/or ranked higher even though that patient is not in spatial proximity to the user's mobile device.

In some embodiments, when a clinical decision support event is subsequently triggered (either automatically or manually in various embodiments) regarding concepts to which the user has subscribed, the validity and then-current active status of the subscribed user's access privileges to the information are once again checked, and, if active and valid, the stored clinical information available for that patient and for the tagged-subscribed concepts that are relevant to the clinical decision support event are accessed. A system-generated link or access-means or message containing the relevant topical, concept-associated clusters of information are presented to the clinician user or to a consumer user. In one embodiment, this information is transmitted to the user's mobile device and presented on the mobile device via application software. Alternatively, the information may be contained in SMS text message or other general-purpose application software resident on the mobile device. In yet other embodiments, the information may be contained in an electronic mail message.

In one embodiment, a method for locating a nearest beacon (such as a Bluetooth Low Energy or BLE beacon) within a plurality beacons in a health services facility comprises (a) identifying a latest highest Received Signal Strength Indication (RSSI) value Bluetooth beacon associated with a highest RSSI value from within a set of latest scanned Bluetooth beacons. The method further includes computing at least one average RSSI value for a predefined number of RSSI value detections associated with at least one Bluetooth beacon within a latest and previous set of scanned Bluetooth beacons. Thereafter, the method includes identifying a highest average RSSI value Bluetooth beacon from within the latest and previous set of scanned Bluetooth beacons.

As described above, some embodiments described herein include an RF beacon, such as a BLE-enabled beacon device. Conventional applications of RF beacons in healthcare settings typically have been directed to recipient users of health care services, such as patient wayfinding and patient check-in and tracking (for example, Connexient, Stanley, MySphera). In contrast, some embodiments described herein may utilize RF beacons for timely provisioning of context-, procedure-, venue-, and role-relevant electronic health record information and diagnostic and therapeutic decision-support to clinician or caregiver users who are providing care to the patient corresponding to the beacon.

In particular, conventional implementations of beacons that are worn or carried by a patient typically send a signal with a beacon identifier effectively saying "It is me, and I am here near you!" However, the enhanced beacons of the present invention may trigger transmission of relevant data related to the beacon bearer (e.g., a target patient affiliation with a plan or protocol; pending actions or decisions; allergies and medications and adherence data) from an electronic health records (EHR) computer system to the clinician's or caregiver's mobile device that detects the beacon. In some embodiments, the RF beacon itself may contain some synoptic salient items of patient care-related information, such as health plan indicia, insurance coverage status, major problem list categories and membership in treatment groups, either in the Minor number code that is part of the beacon device's identifier that is advertised via periodic RF signaling or in optional additional 'tag' codes that are contained in machine-readable storage in the beacon device (flash memory), which may be provided in an initial broadcast or provided subsequently after broadcasting a reference pointer and receiving a response by the mobile device.

Further, merely pushing alerts or offers of information to clinician users without referencing specific to patient data or context, which may include adherence and measurements history, may only result in clinician users' being bombarded with excessive push notifications that distract or cause "alert fatigue". This could induce providers to stop using an app or uninstall the app altogether. By contrast, push content that is timely and has relevant context, such as a reduced set of relevant and/or current information about the patient enables a smart, effective, efficient, personalized interaction between the clinician and the patient.

As described herein, confidentiality and privacy are of special concern with regard to healthcare and must be considered with any active messaging or communication means. In one aspect, embodiments utilizing RF beacons achieve greater privacy compared to RFID or similar technologies because beacon technology affords clinician user control of apps that leverage the beacons. Setting different proximity range/distance for different beacons can be set up by changing the broadcasting power of the beacons. For instance, a default setting may be −8 dBm, which may trigger configured rules (further described below) at approximately 2 meters on a BLE-enabled mobile device receiver. With beacons set to broadcast at 0 dBm power, rules may be triggered at approximately 8 m on the BLE-enabled mobile device receiver. At −16 dBm, rules may be triggered at approximately 0.5 meters. Such differences in proximity settings apply in different venues such as hospital intensive care units, individual exam rooms in physician offices, and group therapy conference rooms in outpatient psychiatry and addictions rehabilitation. Beacon device range settings are therefore germane not only to privacy and confidentiality protection, but also to engineering context-appropriate workflows that avoid presentation of excessively many choices or information that is not timely or in the clinician's or caregiver's immediate context.

In some embodiments, RF beacons may be predominantly enabled by Bluetooth Low Energy (e.g., BLE or Bluetooth 4.0). The beacons may be implemented in different formats, including small coin-cell-powered tag-type devices, USB sticks, etc. Further, software-based beacon capabilities may be built into other devices (e.g., home blood pressure cuffs and glucometers and scales, vending machines, smartphones or tablets, and so forth) as well. BLE draws about 2% of a smartphone's battery capacity in typical clinic visit having clinician-contact connection usage of 10 to 30 min duration, significantly less than the 15-20% that a phone's WiFi would consume of battery power over the same period. Thus under embodiments using BLE technology to access EHR information of patients, a clinician having a typical mobile device, such as a smartphone, may be able to see approximately 40 consecutive patients before recharging the smartphone's battery will be necessary.

Another benefit of embodiments using RF beacon systems is that beacons primarily use mobile devices as the receiver system. Given that mobile devices and cellular networks have become ubiquitous, the receiver network is always-on and continuously connected. On the receiver device a mobile app (such as application 143 described below) may be utilized but, unlike conventional RF beacon systems in retail use-cases, there is no barrier in health plan and health care services venues to achieving high penetration and pervasive coverage. Clinicians in managed care and in accountable care organizations (ACOs) may be required according to the conditions of their employment contract to download a beacon receiver app and turn on location services for that app on their mobile device.

One of the considerable challenges in a conventional beacon deployment scenario is managing a large fleet of beacons, spread across multiple physical locations, grouped into different departments, and having different proximity messages attached to each group. Some embodiments described herein solve this problem of identifying groups of beacons by allocating a set of major numbers to each location and use the designated major number to manage a given group of beacons. For example, a provider organization may designate major number "87221" to the clinic location "West Village" and use that major number for every beacon of every patient whose care is primarily rendered at that clinic. Accordingly, to have a set of beacons trigger the same campaign, these embodiments may use the "UUID+ Major number" in combination to define a "context" and trigger content delivery, such as subscription updates of target patient information, based on that context.

However, even under this approach, this may be other problems. For example, in iOS, an app can only monitor a maximum of twenty regions. In particular, without re-engineering the UUID alone, the app is limited to about 12 'contexts' (analogous to 'regions' in proximity-based beacon-enabled scenario) to work with. Thus using region-type contexts to trigger 'protocols' or 'plans of care' or 'caresets' or 'care tickets' (analogous to 'campaigns' in proximity-based beacon-enabled scenarios) results in coarse-grained control.

Finer-grained control may be necessary in many situations to run personalized-medicine context-related care plans via specific beacons. Using BLE beacon Major numbers allows one to use only one dimension, such as individual identity or physical location, to define the scope of a personalized careset (campaign). In some instances, one may need more than one dimension to define the scope for specific caresets. For example, one may need to run personalized care plans based on patient (e.g., "MRN 1234567" encrypted in the beacon's Major number code or other beacon indicia) and clinical specialty or department (e.g., "mental health") worldwide, to enable context-aware care to be provisioned regardless where the patient presents herself for care. One can use the BLE beacon Major number for location or for department, but not both concurrently. Or one can use Major number as a patient identifier, but not for populations under care that are larger than 65,535 people.

To address these challenges, some embodiments described herein support the notion of "tags" that one can attach to different entities, such as Beacons, Rules, and Cards. Tags are flexible and afford finer-grained control than using beacon Major number control only. In embodiments using tags, As a beacon is deployed, it may be "tagged" with multiple properties concurrently, such as individual and group properties (e.g., the emitted reference pointer may comprise "MRN 1234567", which may be encrypted in the BLE beacon's Major number code and "St. John's bipolar depression group" encrypted in the BLE beacon's Minor number code). Authentication can be provided for wirelessly communicating data and/or services between the mobile device and at least one beacon out of a plurality of beacons and dispersed among patients.

Referring now to the drawings in general, and initially to FIG. 1A in particular, an aspect of an operating environment 100 is provided suitable for practicing an embodiment of the technologies described herein. We show certain items in block-diagram form more for being able to reference something consistent with the nature of a patent specification than to imply that a certain component is or is not part of a certain device. Similarly, although some items are depicted in the singular form, plural items are contemplated as well (e.g., what is shown as one data store might really be multiple data-stores distributed across multiple locations). But showing every variation of each item might obscure the invention. Thus for readability, we show and reference items in the singular (while fully contemplating, where applicable, the plural).

As shown in FIG. 1A, environment 100 includes computing system 130. In some embodiments, computing system 130 includes an adaptive multi-agent operating system, but it will be appreciated that computing system 130 may also take the form of an adaptive single agent system or a non-agent system. Computing system 130 may be a distributed computing system, a centralized computing system, a single computer such as a desktop or laptop computer or a networked computing system. Some embodiments of computing system 130 include computer software stack, such as software stack 121 of FIGS. 1B and 1C, which in some embodiments operates in the cloud, as a distributed system on a virtualization layer within computing system 130. Furthermore, some embodiments of software stack 121 include a distributed adaptive agent operating system as further described in connection with operating system 129 of FIGS. 1B and 1C, which may be implemented as a platform in the cloud, and which is capable of hosting a number of software services, such as services 122-128 described in connection to FIGS. 1B and 1C. Thus, in some embodiments, computing system 130 takes the form of a distributed adaptive-agent computing system or platform, which may further comprise a multi-agent computing system, as described herein.

In some embodiments, computing system 130 comprises a multi-agent computing system. Multi-agent computing system 130 may be used to address the issues of distributed intelligence and interaction by providing the capability to design and implement complex applications using formal modeling to solve complex problems and divide and conquer these problem spaces. Whereas object-oriented systems comprise objects communicating with other objects using procedural messaging, agent-oriented systems use agents based on beliefs, capabilities and choices that communicate via declarative messaging and use abstractions to allow for future adaptations and flexibility. An agent has its own thread of control, which promotes the concept of autonomy.

In some embodiments, agents continually monitor events to proactively detect problems and leverage reasoning to react and dynamically alter a plan. In an embodiment, agents can be leveraged to determine concepts related or associated with the user-selected items of interest about a patient, and then prioritize those related items based on criteria such as user preferences, user history information, which can include information compiled from multiple users, staleness of the information item, condition of the third person, information items in the set of information items, the user device, or a significance-value associated with an information item. Thus for example, one or more agents may be used to determine which concepts a user, such as a healthcare provider, would want to see for a particular patient, given that patient's condition. To facilitate this, the one or more agents might employ information-set logic services 124 of FIGS. 1B and 1C, in one embodiment. Accordingly, only those prioritized items, then, would be provided to the user's mobile device, in this embodiment.

System 130 comprises one or more processors operable to receive instructions and process them accordingly, and may be embodied as a single computing device or multiple computing devices communicatively coupled to each other. In one embodiment, processing actions performed by system 130 are distributed among multiple locations such as a local client and one or more remote servers. In one embodiment, system 130 comprises one or more computing devices, such as a server, desktop computer, laptop, or tablet, cloud-computing device or distributed computing architecture, a portable computing device such as a laptop, tablet, ultra-mobile P.C., or a mobile phone.

Figure 1B:
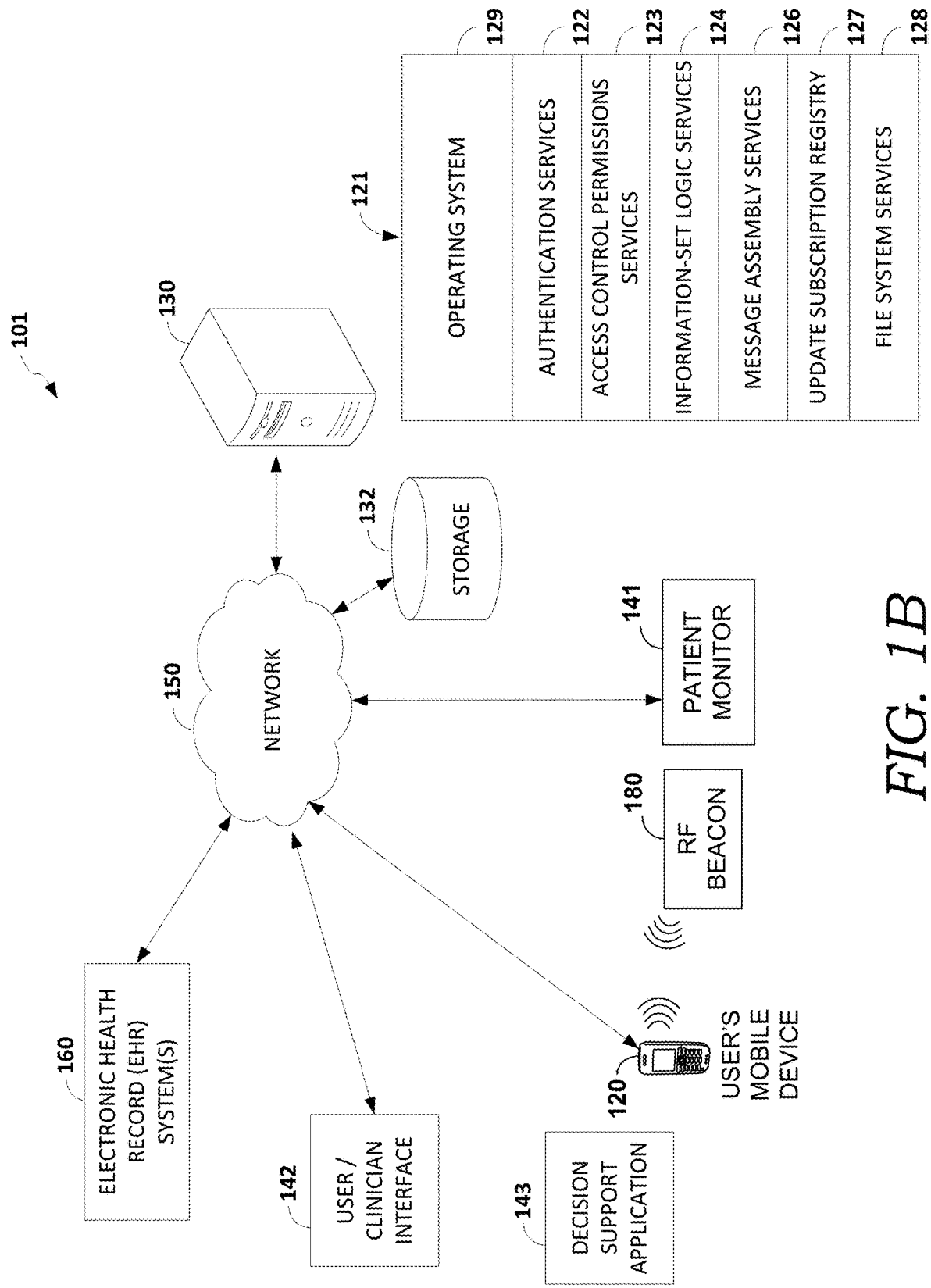
Figure 1C:
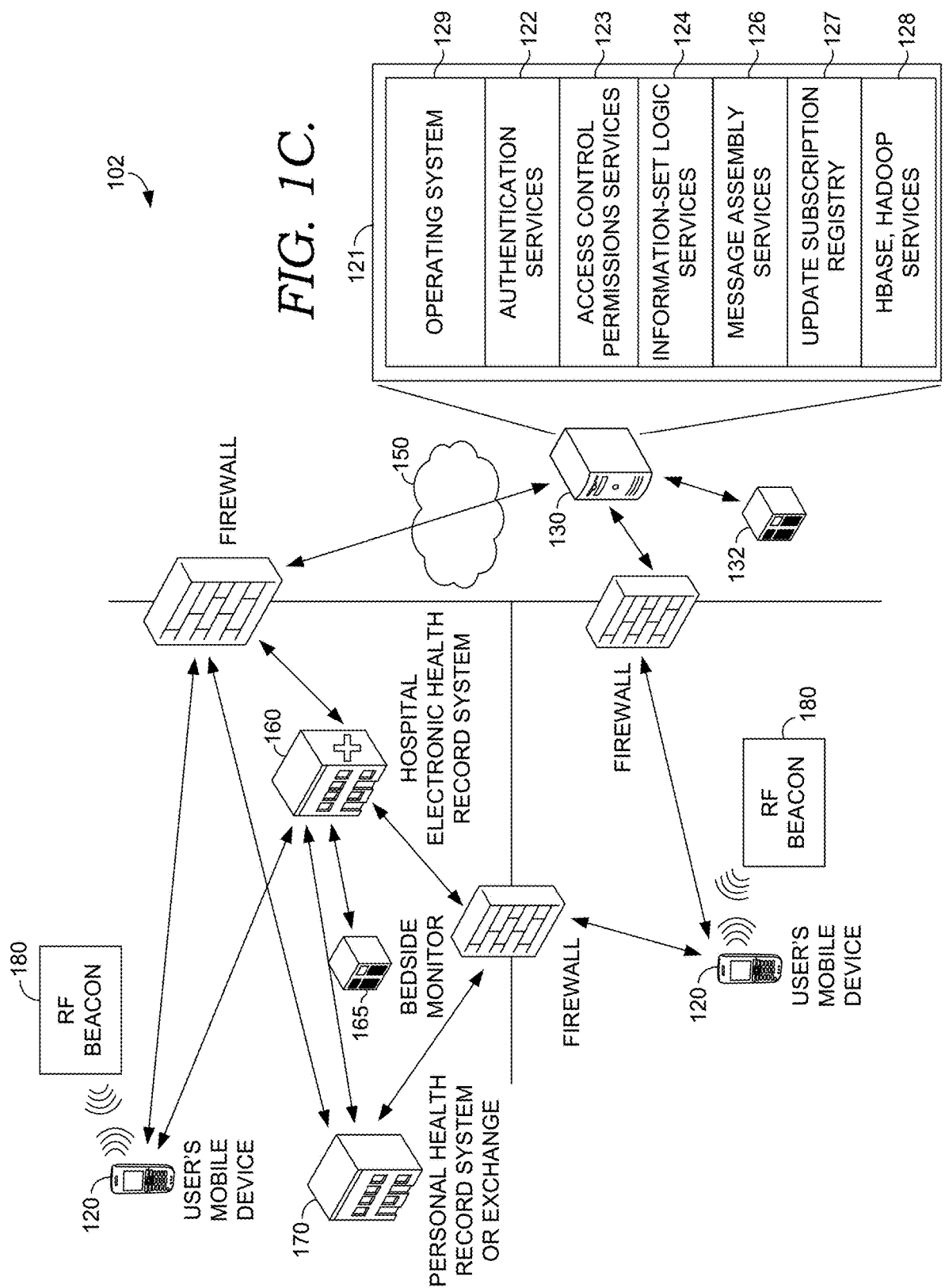
Figure 1D:
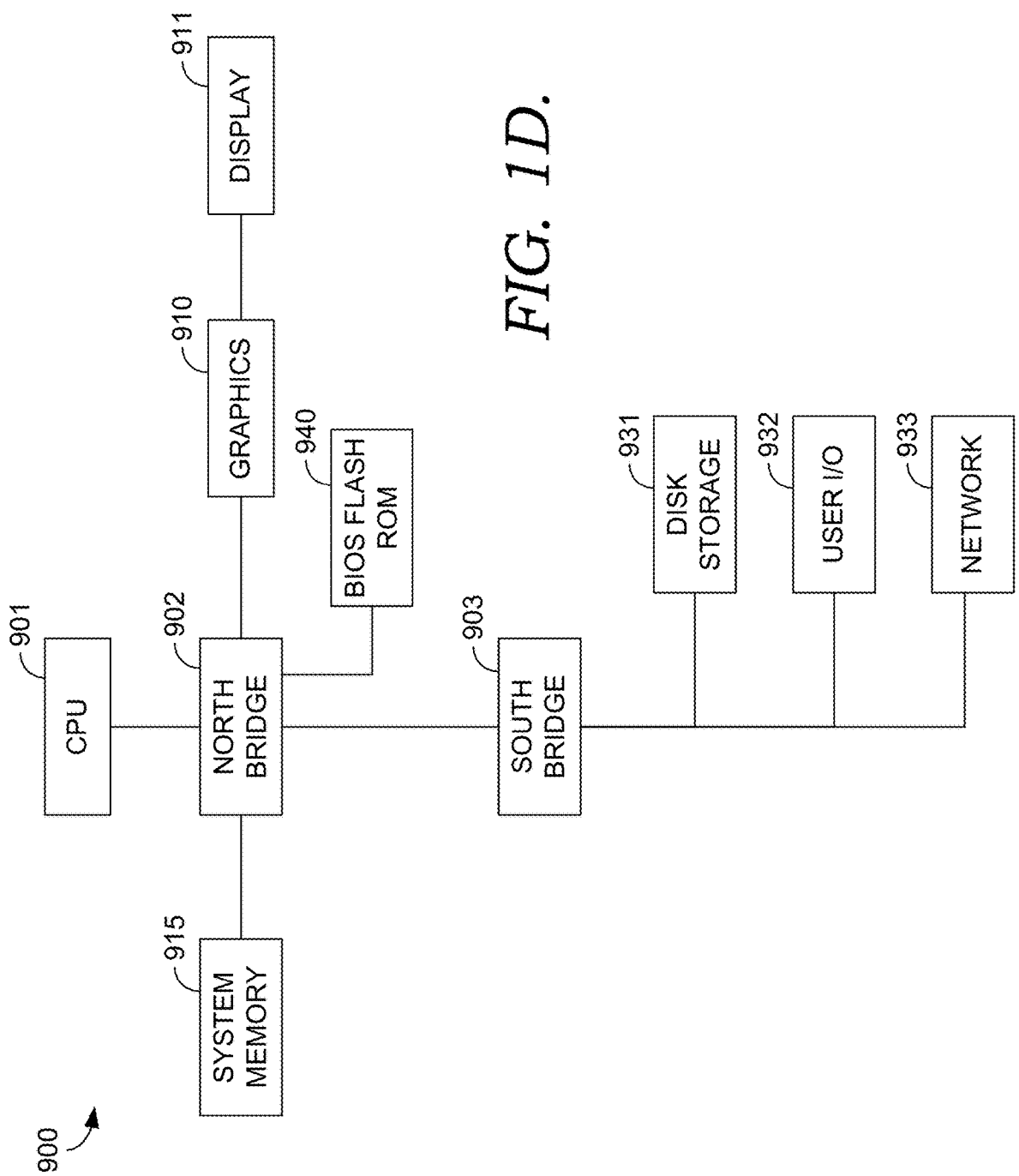

Turning briefly to FIG. 1D, there is shown one example embodiment of computing system 900 that has software instructions for storage of data and programs in computer-readable media. Computing system 900 is representative of a system architecture that is suitable for computer systems such as computing system 130. One or more CPUs such as 901, have internal memory for storage and couple to the north bridge device 902, allowing CPU 901 to store instructions and data elements in system memory 915, or memory associated with graphics card 910, which is coupled to display 911. Bios flash ROM 940 couples to north bridge device 902. South bridge device 903 connects to north Bridge device 902 allowing CPU 901 to store instructions and data elements in disk storage 931 such as a fixed disk or USB disk, or to make use of network 933 for remote storage. User I/O device 932 such as a communication device, a mouse, a touch screen, a joystick, a touch stick, a trackball, or keyboard, couples to CPU 901 through south bridge 903 as well. The system architecture depicted in FIG. 1D is provided as one example of any number of computer architectures, such as computing architectures that support local, distributed, or cloud-based software platforms, and are suitable for supporting computing system 130.

In some embodiments, computing system 900 is a computing system made up of one or more computing devices. In an embodiment, computing system 900 includes an adaptive multi-agent operating system, as described above, but it will be appreciated that computing system 900 may also take the form of an adaptive single agent system or a non-agent system. Computing system 900 may be a distributed computing system, a data processing system, a centralized computing system, a single computer such as a desktop or laptop computer or a networked computing system.

Returning to FIG. 1A, computing system 130 is communicatively coupled to information store or storage 132, described below, and communication network 150. Communication network 150 comprises a network or set of communicatively coupled networks that enable data and computer instructions to be communicated among the systems and devices coupled to the communication network 150. In an embodiment, network 150 includes the Internet, and may also include one or more intranets, which may be public or private. In some embodiments, network 150 comprises a cloud-computing network, which is known in the art as "the cloud" and may also include computing system 130. In an embodiment, network 150 includes a telecommunication network for communicating with a mobile device, such as a mobile phone.

Continuing with the embodiment depicted in FIG. 1A, communication network 150 is communicatively coupled to mobile device 120, server 140, Electronic Health Record Information system (EHR) 160, and Health Record Exchange, (HRE) 170; each of which is described below. In one embodiment, mobile device 120 is a mobile phone or tablet device able to receive data for example, SMS text messages, email, instant messages, or other data, and present information, or an indication that information is available, to a user. In one embodiment, mobile device 120 is a smart phone, such as an Apple iPhone®, that includes an application program (an example of which is described in connection to FIG. 1B), referred to as an "app." The app facilitates receiving the reference pointer, which in one embodiment comprises a communicated identifier or beacon, such as a BLE-type beacon comprising a UUID and/or and associated major and minor codes, additional tag codes and/or metadata, and presents information items, such as information about a third-party patient, to the user. In one embodiment, the app also provides user credentials for identification or authentication of the user, to server 140. In one embodiment, mobile device 120, or an app running on mobile device 120, is capable of communicating via a short-range RF protocol such as Bluetooth 4.0, ANT+, or other close-proximity RF protocol oriented to beacon-type signaling. Further embodiments of the app are discussed below in connection to FIGS. 1B and 5.

In some embodiments, as further described below, a user can be authenticated as a medical provider authorized to receive medical data based on a location of the user near the at least one beacon transponder located in association with a patient for which the medical data is provided. Mobile device 120 may be configured to enable the medical provider to record a medical procedure as a video via a digital camera (e.g., video cameras) integrated with the mobile device and make medical annotations while treating the patient. Such annotations can be voice annotations recorded by the mobile device. The annotations and the video can be securely stored in a server 1240 and/or as a medical record in an electronic health record system 160 in association with the patient and can be made available for subsequent retrieval by authorized medical providers. In some embodiments mobile device 120 may be capable of bidirectional communication with a second screen or user interface in order to provide a larger viewing platform of the data and/or the services. In these embodiments, the second screen can be a display screen located within viewing proximity of the mobile device 120. Such a second screen can be, for example, be another computing a device such as a display screen of a smartphone, a laptop computer, a tablet computing device, a flat panel television, and a projector.

Server 140 receives requests originating from mobile device 120, for information identified by the reference pointer, such as subscribed-to information about a third-party patient, and provides that information, or a portion of that information, to the mobile device. In an embodiment, server 140 communicates with mobile device 120 through a mobile-device network, such as AT&T, Sprint, or Verizon, for example. In one embodiment, server 140 is included in computing system 130, and in one embodiment, server 140 is distributed across two or more computing system 130, EHR 160, and a mobile device network. Thus, in some embodiments, server 140 may be distributed into any component that received a request for information from mobile device 120 and provides information to mobile device 120. Likewise, in some embodiments, computing system 130 includes server 140.

EHR 160 comprises the healthcare provider record system or electronic health record information, which in one embodiment includes electronic health records or medical records for a patient, a collection of patients, or a population. Additional examples of EHR 160 are described in FIG. 1B. HRE 170 comprises a health record exchange.

Example operating environment 100 depicted in FIG. 1A further includes a patient-monitor 165 and RF Beacon 180. Monitor 165 determines various physiological levels of a patient, such as for example, cardio and respiratory information. In one embodiment, monitor 165 takes the form of a bedside monitor such as bedside monitor 165 shown in FIGS. 1B and 2B, such as may be found in a hospital for monitoring a patient's vital signs. In one embodiment, monitor 165 comprises a sensor or set of sensors worn by the patient. In one embodiment, monitor 165 is embodied as any patient monitor for monitoring information about a patient, such as patient monitor 141 shown in FIGS. 1B and 2A, and further described in FIG. 1B.

In one embodiment, RF Beacon 180 comprises a wireless-communication apparatus worn on, carried about, or otherwise located in proximity to or on the person of a target, such as a patient. RF Beacon 180 is configured to be capable of emitting RF signals having a modest range, which may be configurable such as from 1 meter to as much as 70 meters or more, indicating a physical proximity of the patient to one or more nearby wireless-communications enabled (such as BLE-enabled) mobile devices 120. In one embodiment, RF beacon 180 is capable of broadcasting a beacon that may be used to identify a particular nearby target (such as a patient) corresponding to the beacon and/or may be used to determine other information about the target, such as information corresponding to a plan or treatment group membership affiliations that are in-effect for the patient, and/or other care-related information.

It should be noted that there are differences between location and proximity use-cases. In particular, location-determining technologies may utilize GPS, cell tower geo-location, WiFi, IP or MAC address (e.g., geoIP) for use cases such as driving directions, weather and atmospheric AQI exposures. Such technologies typically have a spatial resolution of tens of meters to kilometers. It is contemplated that some embodiments may utilize these technologies. But in contrast to location-determining technologies, proximity-determining technologies may utilize BLE, iBeacon, ANT+, RFID, or similar technologies and are more suitable for patient tracking, patient check-in, context-aware EHR information provisioning, and clinical decision support, and many of the other embodiments described herein. Such technologies typically have a spatial resolution of tens of centimeters to meters.

In some embodiments, as described herein, a caregiver-user or provider-user who is authorized to know of such target-patient information may be notified in near-realtime of the proximity of the patient and of the availability of said information on the user's BLE-enabled (or wireless-communications enabled) mobile device. Examples of RF Beacon 180 are shown in FIGS. 6A-6C. In particular, with reference to FIGS. 6A-6C, RF beacon 180 may take the form of a credit-card-size "tag" (FIG. 6A), or a miniature beacon disc (FIGS. 6B and 6C), or may be embodied as a computer, tablet computer, a mobile device such as a smartphone or other wireless-communication-enabled computing device, or any similar device capable of implementing beacon communications. RF Beacon 180 may be a single device or a may be a combination of devices, such as a beacon disc plus the patient's smartphone, or such as a beacon disc plus a wearable monitoring device such as an exercise tracker or heartrate-measuring smartwatch, and may be stationary or mobile. In some cases, the beacon may be comprised of one component that is mobile (such as a beacon disc that is worn or carried by the patient) and another component that is stationary (such as a BLE-enabled digital bathroom scale or blood pressure cuff).

One example of a beacon that can be implemented in accordance with one or more embodiments described herein is the "iBeacon." iBeacon is the trademark for the proximity system that Apple Inc. has referred to as "a class of low-powered, low-cost Bluetooth transmitters that can notify nearby iOS devices of their presence." The technology enables an iOS device or other hardware to send push notifications to iOS devices that are in close proximity, up to approximately 100 meters. Devices running the Android operating system, for example, can receive iBeacon advertisements but cannot emit iBeacon advertisements (i.e., embody a BLE 'central' role only and cannot serve as BLE 'peripherals'). Currently, the iBeacon operates on Bluetooth Low Energy (BLE), also known as Bluetooth Smart. BLE is also found on Bluetooth 4.0 devices that support dual mode. iBeacon uses Bluetooth low energy Proximity sensing to transmit a universally unique identifier (UUID) capable of being received by a compatible app or operating system that can be turned into a physical location or trigger an action on the receiving device.

Returning to FIG. 1A and with reference to FIGS. 1B and 1C, which also include RF Beacon 180, in some embodiments RF Beacon 180 is capable of communicating user information to a mobile device 120, which may be encoded as a reference to other information (i.e., a reference pointer) that identifies the set of information items related to a subscription or interest identified by a user, as described herein. As described above, in some embodiments, RF beacon 180 communicates information such as a reference pointer or identifier that functions as a reference to identify a target (e.g., a patient) associated with the RF beacon. In some embodiments, RF beacon 180 communicates information identifying the particular RF beacon, which is associated with the target (e.g., a particular patient) and thus references or points to information about the target. Thereafter, an app or other software on mobile device 120 may be used to determine a particular patient (or other target) identified by the information received from the RF beacon 180. The communication from the RF beacon 180 may be broadcasted, such as periodically, at intervals, or continuously or may be provided in response to a communication from the user mobile device 120. For example, user mobile device 120 may emit a signal or ping to awaken and identify RF beacons 180 in spatial proximity (such as within wireless communication range) of the user mobile device 120. In some embodiments, triggering rules and corresponding actions (described below) may be used to detect a particular beacon and/or to provide a certain information to a subscribing user or beacon-detecting mobile device.

Some embodiments herein may employ beacon context monitoring. A beacon context is a logical space which is formed by union of contexts (regions) of all beacons with same UUID or identifier and Boolean combination of Major number, Minor number, and, optionally, Tags. Some embodiments may be configured to monitor entering and exiting from Beacon context while a monitoring feature of an app (such as application 143 of FIG. 1C) is running in the foreground or, alternatively, is running in the background mode. Whenever the clinician or caregiver user enters or exits a beacon context, a communications service may send a callback to the app along with the identifier for the context. Beacon context monitoring is useful in identifying when the user is entering or exiting a venue where one beacon is present, such as an exam room where a single beacon-bearing patient is situated, or a venue where multiple beacons that bear a contextual relationship to each other are deployed, such as a conference room where the clinician user is presiding over a group therapy session for multiple patients concurrently.

Some embodiments herein may employ beacon ranging. Beacon ranging is a process of detecting the individual beacons 180 which are detectable by mobile device 120 inside a beacon context. For example, if there are 5 beacons currently present in a clinic or physician's office, the ranging call back from the communications service may return a list of all the 5 beacons along with their respective signal strength. This is useful in identifying relative distance from each beacon and automatically giving focus to the EHR information for the individual patient whose beacon is nearest. Alternatively, the clinician may manually bind to the EHR information of a patient associated with another beacon who is further away (or who is nearer but whose battery is more depleted than one or more other beacons; or whose bearer's clothing or purse or other objects partially obstructs the signal from that bearer's beacon, which therefore has a lesser signal strength for the mobile device of the clinician).

Figure 7:
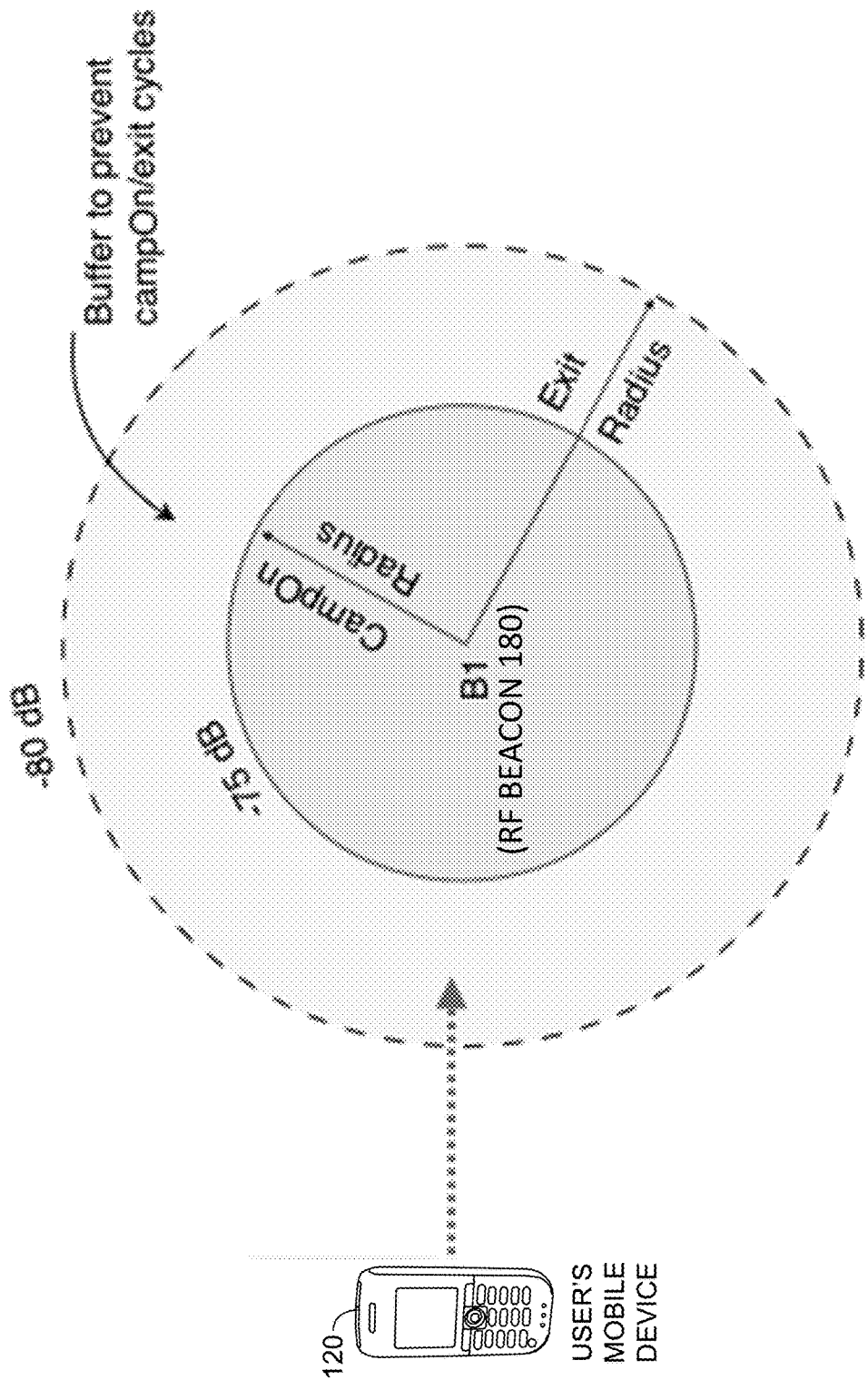
FIG. 7 shows an example scenario of region entry and exit for an RF beacon (B1) and corresponding mobile device used to detect the beacon, in accordance with an example embodiment of the disclosure.

Some embodiments described herein may utilize a beacon camp-on/exit feature. In particular, the capability of beacon camp-on enables determining if a clinician or caregiver user (carrying a mobile device 120) has spent enough time within proximity of a beacon and, if so, declare the persistent proximity to be a camp-on connection to this particular beacon 180. In venues where the mobile device can range more than one beacon, a communications service may heuristically determine which of the beacons is sufficiently near to the user to constitute a potential group or beacon cluster. When proximity establishes a potential cluster, the attribute tags may be examined by the app to determine what Boolean intersections of attribute values exist among the beacons, if any. The discovery of one or more non-null intersections may cause the app to retrieve information pertaining to the discovered cluster or group. When the communications service notices that the user has moved significant distance from the beacon(s) and sufficient time has passed for the user to be unlikely to resume spatial proximity to the beacon(s), the communications service asserts a beacon exit. In both the cases, a delegate callback is sent from the communications service to the app along with reference to the beacon and the message corresponding to the camped-on beacon only needs to be displayed to the user. In the example of an outpatient health care clinic or physician office suite, if one beacon is carried or worn by various beacon-bearing patients, the communications service camps-on to individual patient beacons as the clinician user moves from one exam room to another. The corresponding relevant EHR media is displayed to the user one patient at a time, with no ambiguity about which patient and beacon are of interest at each moment. FIG. 7 shows an example of a region entry/exit CampOn function, which may be used in the above examples. In particular as mobile device 120 enters signal range of RF beacon 180 (designated as B1), proximity within the CampOn radius (here, within −75 dB) must occur before a connection may occur to beacon B1 and thus a reference pointer received by the mobile device 120. In some embodiments, a larger buffer radius between −75 and −80 dB may be employed to prevent CampOn/Exit cycles for occurring unwantedly.

Returning to FIG. 1A, environment 100 also includes information store 132. Information store 132 stores information including data and executable code used to facilitate providing mobile-device updates of electronic health records. In some embodiments, this information includes, for example, user subscription information or information otherwise identifying a set of information items related to the information items indicated by the user; user-access permissions or authentication information; mobile-device identification codes; patient health records; healthcare provider records; parameters used by a distributed adaptive agent operating system including, for example, criteria for identifying and prioritizing the set of information items related to the information items indicated by a user; rules engine(s) and associated parameters for determining which information to provide to a mobile-device based on the indication received by a user; and user preferences.

Although shown as a single information store, information store 132 may comprise multiple separate dedicated information stores. For example in one embodiment EHR 160 may have a dedicated information store. In some embodiments, information store 132 comprises networked storage or distributed storage including storage on servers located in the cloud. Thus, it is contemplated that for some embodiments, the information stored in information store 132 is not stored in the same physical location. For example, in one embodiment, one part of information store 132 includes one or more USB thumb drives or similar portable data storage media. Additionally, in some embodiments, data stored in information store 132 can be searched, queried, analyzed using system 130 or user/clinician interface 142 (described in FIG. 1B), which may be embodied within a software app running on mobile device 120 (such as application 143 described in FIG. 1B). In embodiments where information store 132 is distributed, portions of information stored in store 132 may be logically located behind a firewall or otherwise have limited access or require security validation for access.

Turning to FIGS. 1B and 1C, exemplary operating environments 101 and 102 are provided, respectively, and depict operating environments suitable for practicing some embodiments described herein. Operating environments 101 and 102 include many of the components of operating environment 100 described above in connection to FIG. 1A, and provide additional perspectives of aspects of suitable example operating environments. Just as with operating environments 100, other arrangements and elements can be used in addition to or instead of those shown in operating environments 101 or 102, and some elements may be omitted altogether for the sake of clarity. Further, as with operating environment 100, many of the elements described herein are functional entities that may be implemented as discrete or distributed components or in conjunction with other components, and in any suitable combination and location.

As described herein, some embodiments may be implemented as a system, comprising one or more computers and associated network and equipment, upon which a method or computer software programs or application(s) are executed. Accordingly, aspects of the present disclosure may take the form of an embodiment combining software and hardware aspects that may all generally be referred to herein as a "module" or "system." Further, the methods of the present disclosure may take the form of a computer application embodied in computer readable media having machine-readable application software embodied thereon. In this regard, a machine-readable storage media may be any tangible medium that can contain, or store a software application for use by the computing apparatus.

Computer application software for carrying out operations for system components or steps of the methods of the present disclosure may be authored in any combination of one or more programming languages, including an object-oriented programming language such as Java, Python, R, or C++ or the like. Alternatively, the application software may be authored in any or a combination of traditional non-object-oriented languages such as C or Fortran. The application may execute entirely on the user's computer as an independent software package, or partly on the user's computer in concert with other connected co-located computers or servers, or partly on the user's computer and partly on one or more remote computers, or entirely on a remote computer or collection of computers. In the latter cases, the remote computers may be connected to the user's computer through any type of network, including a local area network (LAN) or a wide area network (WAN), or the connection may be made to an external computer (for example, via the internet using an Internet Service Provider or ISP) or an arbitrary, geographically-distributed, federated system of computers, such as a cloud-based system.

Moreover, the components of operating environments 100, 101 and 102, functions performed by these components, or services carried out by these components may be implemented at appropriate abstraction layer(s) such as the operating system layer, application layer, hardware layer, etc., of the computing system(s). Alternatively, or in addition, the functionality of these components and/or the embodiments described herein can be performed, at least in part, by one or more hardware logic components. For example, and without limitation, illustrative types of hardware logic components that can be used include Field-programmable Gate Arrays (FPGAs), Application-specific Integrated Circuits (ASICs), Application-specific Standard Products (ASSPs), System-on-a-chip systems (SOCs), Complex Programmable Logic Devices (CPLDs), etc. Additionally, although functionality is described herein with regards to specific components shown in example environment 101, it is contemplated that in some embodiments functionality of these components can be shared or distributed across other components.

With reference to FIG. 1B, example operating environment 101 includes one or more electronic health record (EHR) systems, such as EHR system(s) 160 communicatively coupled to network 150, which is communicatively coupled to computer system 130. In some embodiments, components of environment 101 that are shown as distinct components may be embodied as part of or within other components of environment 101. For example, EHR system(s) 160 may comprise one or a plurality of EHR systems such as hospital EHR systems, health information exchange EHR systems (such as health information exchange 170 shown in FIGS. 1A and 1C), clinical genetics/genomics systems, ambulatory clinic EHR systems, psychiatry/neurology EHR systems, insurance, collections or claims records systems; and may be implemented in or as a part of computer system 130. Similarly, EHR system(s) 160 may perform functions for two or more of types of EHR systems (not shown). EHR system(s) 160 also may include records of physiological variables or other patient information obtained via one or more measurement apparati, tests, or screenings, such as patient monitor 141 (or bedside monitor 165 of FIGS. 1A and 1C), and may perform functions for two or more of types of EHR systems (not shown). In an embodiment, EHR system(s) 160 includes historical claims data for health services, apportionment data, and related health services financial data.

In some embodiments of the technologies described herein, aspects of decision support for patient care may utilize data about a population of patients derived from patient EHR or other records information. In particular, presently certain data warehouses are created for purposes of public health and observational research purposes and are derived from electronic health records repositories in such a way that they are de-identified so as to comply with applicable confidentiality laws and regulations. The Cerner Health Facts™ data warehouse is such a system that has been curated for more than 15 years. It comprises a large 'transaction database' where each entry corresponds to a patient's 'basket' (a collection of items recorded or transacted at points in time during episodes of care services provisioning in the contributing health care institutions). Each database entry is ordered by the date-time of the transaction. Transaction sequencing is implemented by grouping medical events occurring in the same 'epoch' for the same patient together into 'baskets' and ordering the 'baskets' of each patient by the date-time stamps where the events occurred. Epoch durations may differ according to the age of the patient, or the acute or chronic nature of the health conditions that pertain to the patient, or the rate of change of the severity of the health conditions, or other factors, Epoch durations may be as short as a few minutes (as in critical care ICU or operating room contexts) or may be as long as 10 years or more (as in chronic ambulatory care-sensitive conditions, ACSCs).

Continuing with FIG. 1B, network 150 may comprise the Internet, and/or one or more public networks, private networks, other communications networks such as a cellular network, or similar network(s) for facilitating communication among devices connected through the network. In some embodiments, network 150 may be determined based on factors such as the source and destination of the information communicated over network 150, the path between the source and destination, or the nature of the information. For example, intra-organization or internal communication may use a private network or virtual private network (VPN). Moreover, in some embodiments items shown communicatively coupled to network 150 may be directly communicatively coupled to other items shown communicatively coupled to network 150.

In some embodiments, operating environment 101 may include a firewall (such as depicted in FIG. 1C) between a first component and network 150. In such embodiments, the firewall may reside on a second component located between the first component and network 150, such as on a server 140 (not shown in FIG. 1B), or reside on another component within network 150, or may reside on or as part of the first component.

Embodiments of electronic health record (EHR) system(s) 160 include one or more data stores of health-related records, which may be stored on storage 132, and may further include one or more computers or servers that facilitate the storing and retrieval of the health records. In some embodiments, EHR system(s) 160 and/or other records systems may be implemented as a cloud-based platform or may be distributed across multiple physical locations. EHR system(s) 160 may further include record systems, which store real-time or near real-time patient (or user) information, such as wearable sensor or monitor 141, bedside, laboratory, or in-home patient monitors (e.g., bedside monitor 165 of FIGS. 1A and 1C) or sensors, for example, such as monitor 141.

Example operating environment 101 further includes a user/clinician interface 142 communicatively coupled through network 150 to an EHR system 160. In some embodiments, user/clinician interface 142 also may be directly or indirectly communicatively coupled to RF beacon 180 (not shown). For example, as further described herein, in some embodiments, user/clinician interface 142 may be part of an application, such as decision support application 143, and may reside on mobile device 120 (or may be a cloud-based application accessed via mobile device 120) for viewing information about a patient identified via information receive d from RF beacon 180. Similarly, user/clinician interface 142 may be communicatively coupled to RF beacon 180 for assigning RF beacon 180 to a particular patient (or other target) or for configuring settings or parameters, or receiving diagnostic or status information about the RF beacon 180, such as battery life, communication range (e.g., broadcast power), or operational settings (e.g., how often to broadcast or a particular protocol or encoding scheme for a reference pointer information communicated by RF beacon 180).

As described previously, some embodiments of mobile device 120 include a decision-support software application 143 or app for receiving information from RF beacon 180 and using that information to receive additional, relevant information about a target identified by RF beacon 180. In one embodiment, software application 143 or app is includes or operates in conjunction with user/clinician interface 142, and comprises a software application, or set of applications (which may include programs, routines, functions, or computer-performed services) residing on a client computing device such as mobile device 120 (or distributed in the cloud and/or on other client computing device) such as a personal computer, laptop, smartphone, tablet, or other mobile computing device. In an embodiment, the application 143 is a Web-based application or applet, and may be used to provide or manage user services provided by an embodiment of the technologies described herein, such as to facilitate receiving target-reference information from RF beacon 180 and then receiving additional relevant information referenced by the information received from RF beacon 180. In some embodiments, application 143 comprises a computerized decision support tool and may include aspects of user/clinician interface 142.

In some embodiments, application 143 and/or user/clinician interface 142 facilitates accessing and receiving information from a user or health care provider about a specific patient or set of patients, according to the embodiments presented herein. Embodiments of application 143 and/or user/clinician interface 142 also may facilitate accessing and receiving information from a user or health care provider about a specific patient, caregiver, or population including historical data; health care resource data; variables measurements, timeseries, and predictions (including plotting or displaying the determined outcome and/or issuing an alert) described herein; or other health-related information, and facilitates the display of results, recommendations, or orders, for example. In an embodiment, application 143 and/or user/clinician interface 142 also facilitates receiving orders, staffing scheduling, or queries from a user, based on the results of monitoring and/or forecasted outputs, which may in some embodiments utilize user/clinician interface 142.

In particular, user/clinician interface 142 facilitates receiving from a user, an indication of a particular topic, concept or group of interrelated concepts for which the user, or another user, desires to receive updated information. For example, in one embodiment, user interface 142 is capable of receiving a selection by a user of items of interest about a third-party patient, for which the user desires to monitor by receiving updates of information related to the selected items of interest on the user's mobile device. In some embodiments, user/clinician interface 142 may be embodied as a touch screen, a display, an electronic clipboard or chart, tablet computer, laptop computer, bedside patient monitor, a mobile device, or any similar device capable of receiving input from a user of items of interest about a patient, topic, or concept, including for example a speech-recognition user interface. Interface 142 may be a single display on a single device or a combination of devices, which may be distributed at different locations, and may be stationary or mobile.

One embodiment of interface 142 takes the form of a graphical user interface and application, which may be embodied as part of a software application (e.g., a decision support application 143 operating on or accessed via mobile device 120) operating on one or more mobile computing devices, tablets, smartphones, front-end terminals in communication with back-end computing systems, laptops, or other computing devices. In an embodiment, the application includes the PowerChart® software manufactured by Cerner Corporation. In an embodiment, user/clinician interface 142 includes a Web-based application (which may take the form of an applet or app) or set of applications usable to manage user services provided by an embodiment of the technologies described herein.

Figure 4C:
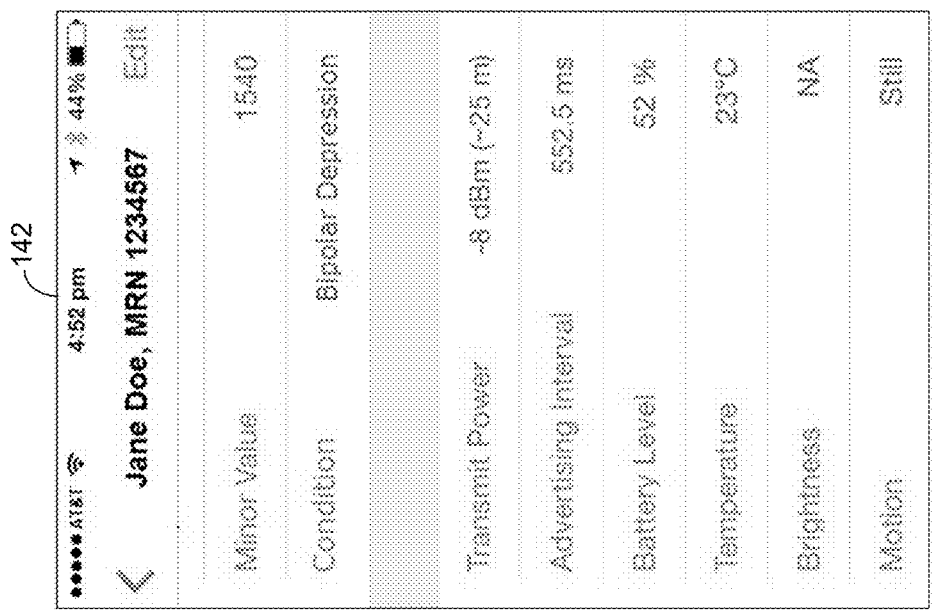

In some embodiments user/clinician interface 142 and/or application 143 is configured to display information about an RF beacon 180. For example, this may include information concerning the beacon's battery status, RF signal strength, and clinical conditions or treatments groups that are associated with this beacon for the beacon's bearer/user. FIG. 4C depicts an example user/clinician interface 142 on a mobile device 120 (not shown) for ascertaining the properties of a BLE beacon (here the beacon is associated with a patient Jane Doe), for purposes of device parameters review and/or troubleshooting. In one embodiment, interface 142 and/or application 143 is configured to display information associated with a beacon's periodic RF broadcasts of its presence to mobile-devices 120 or other wireless-communication enabled devices for detecting the beacon in the vicinity. In some embodiments, a graphic may be presented comprising a 2-D trend plot that contains information related to current or power expenditure during periods of quiescent, receiving, and transmitting operation, such as shown in FIGS. 8A and 8B.

Figure 8A:
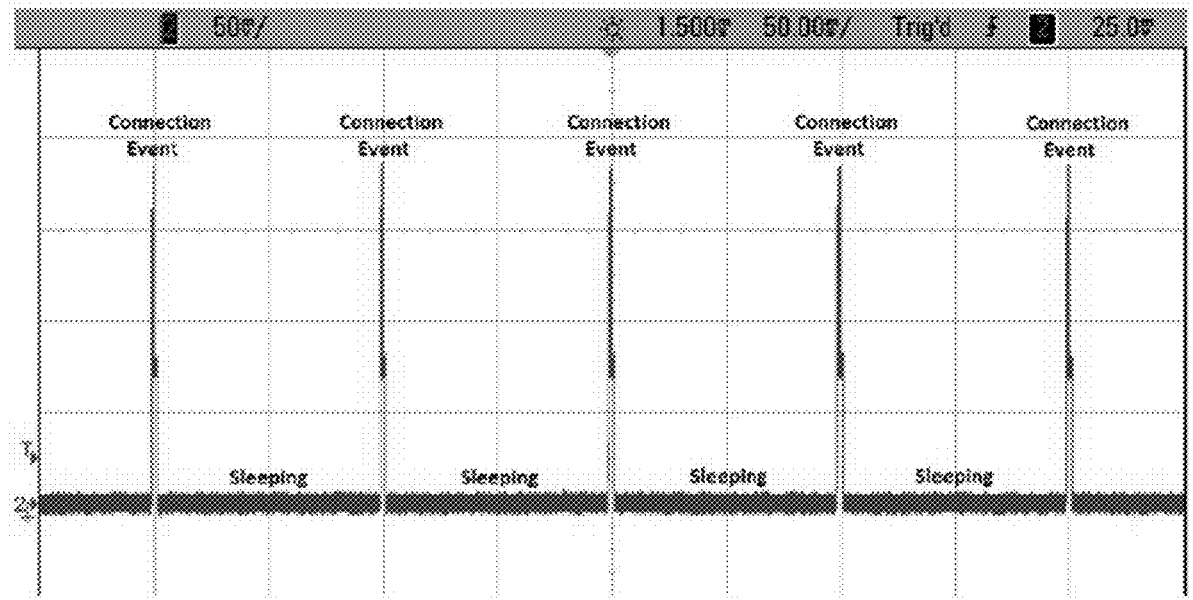
FIGS. 8A and 8B depict aspects of operational states of an example BLE beacon, in accordance with an embodiment of the disclosure.
Figure 8B:
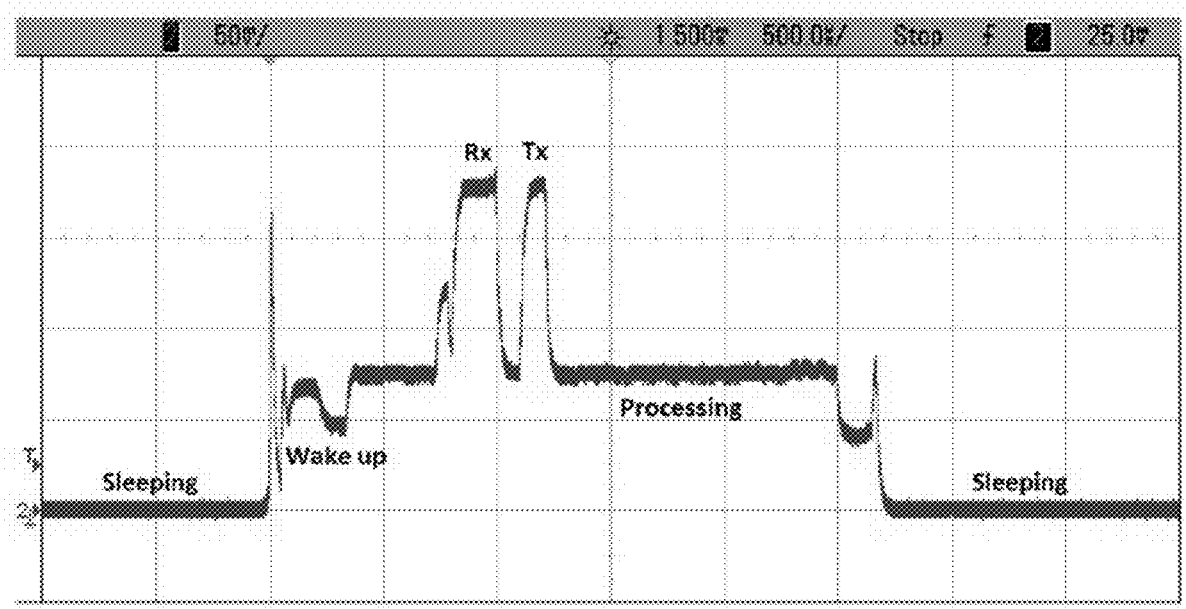

With reference to FIGS. 8A and 8B, an example user interface 142 operating on an application 143 is shown. In this example embodiment, application 143 is configured to monitor the current or power expenditure of a BLE-type beacon during transitions from sleeping mode to connection mode, and, during connection periods, amongst quiescent, wake-up, receiving, transmitting, and processing states, for purposes, of device operations monitoring and troubleshooting. Collectively, information of these types facilitate review of the beacon's operation and troubleshooting of faults or failures in said operation.

Returning to FIG. 1B, in some embodiments, the user interface 142 includes a pushbutton-style switch on a miniature beacon disc to enable placement of the beacon disc into an "Airplane Mode" discontinuing RF transmissions while in aircraft or other locations where RF signaling is prohibited, and in one embodiment, user interface 4B includes other input means such as a keyboard, mouse, pad, voice-recognition module, or other means for receiving, from a user, an indication of information items or commands.

Example operating environment 101 includes patient monitor 141 communicatively coupled through network 150 to an EHR system 160. In an embodiment, patient monitor 141 communicates via network 150 to computer 130, mobile device 120, and/or user/clinician interface 142. The term monitor is used broadly herein, and it is contemplated that in some embodiments, monitor 141 may not perform monitoring but may receive information about physiological parameters which may be measured, observed, or otherwise recorded. Embodiments of monitor 141 may comprise one or more sensors, an interface component, and/or processing/communications component (not shown). In an embodiment of monitor 141 comprises one or more sensor components operable to acquire clinical or physiological information about a patient, such as various types of physiological measurements, physiological variables, or similar clinical information associated with a particular physical or mental state of the patient, and which may be acquired periodically, continuously, as needed, or as they become available, and may be represented as one or more time series of measured variables. In one embodiment, monitor 141 comprises sensors for obtaining (and in some instances pre-processing or interpreting) non-invasive recording of vital signs, which may be obtained continuously, periodically, or at irregular intervals. For example, in an embodiments monitor 141 comprises a patient monitoring system such as Sotera ViSi®, Finapres® NOVA™, or Covidien ZephyrLIFE™. In some embodiments, monitor 141 comprises patient bedside monitor, such as bedside monitor 165 of FIGS. 1A and 1C, which may be used in a hospital setting. In an embodiment, one or more sensor components of monitor 141 may comprise a user-wearable sensor component or sensor component integrated into the patient's environment. Examples of sensor components of monitor 141 include a sensor positioned on an appendage (on or near the user's head, attached to the user's clothing, worn around the user's head, neck, leg, arm, wrist, ankle, finger, etc.); skin-patch sensor; ingestible or sub-dermal sensor; sensor component(s) integrated into the user's living environment (including the bed, pillow, or bathroom); and sensors operable with or through a smartphone carried by the user, for example. It is also contemplated that the clinical or physiological information about patient, such as the monitored variables and/or clinical narratives regarding the patient, used according to the embodiment of the invention disclosed herein may be received from human measurements, human observations, or automatically determined by sensors in proximity to the patient. For example, in one embodiment, a nurse periodically measures a patients' blood pressure and enters the measurement and/or observations via user/clinician interface 142. In another example, a nurse or caregiver enters one or more progress notes for an in-patient via user/clinician interface 142. Similarly, values for vital signs variables may be entered via user/clinician interface 142.

Examples of physiological variables monitored by monitor 141 can include vital signs variables, such as heart rate (bradycardia and tachycardia) and blood pressure (hypotension and hypertension) and oxygen saturation (peripheral desaturation), as described herein. Additionally, in some embodiments physiological variables monitored by monitor 141 may include, by way of example and not limitation, central venous pressure, other vital signs or any type of measureable, determinable, or observable physiological or clinical variable or characteristic associated with a patient, which in some embodiments may be used for forecasting a future value (of the measured variable, a composite variable based on one or more measured variables, or other factor determined at least in part from one or more measured variables) of a patient in order to facilitate clinical decision making In an embodiment, a monitor such as 141 comprises a sensor probe, such as an EEG probe, and a communication link that periodically transmits identification information and probe data to EHR 160, so that the time series of monitored values is stored thereby enabling the patient manager to determine a physiological variable decision statistic. In an embodiment, monitor 141 collects raw sensor information, such as optical sensor 184, and performs signal processing, such as velocity measurement, forming a physiological variable decision statistic, cumulative summing, trending, wavelet processing, thresholding, computational processing of decision statistics, logical processing of decision statistics, pre-processing or signal condition, etc., part or all of which may be performed on monitor 141, user/clinician interface 142, and/or computer system 130.

Embodiments of monitor 141 may store user-derived data locally or communicate data over network 150 to be stored remotely. Some embodiments of monitor 141 include a monitor interface, which may be embodied as user/clinician interface 142 or a separate monitor user interface, and may further include I/O such as buttons and sounds emitted from the monitor 141, its firmware or software application or app operating on a user's mobile device 120 or computer system 130, and in an embodiment may facilitate uploading of measured (or recorded, or otherwise received) information from measurement device 141 to EHR 160 or computer system 130.

Additionally, some embodiments of monitor 141 include functionality for processing patient-derived information locally or for communicating the information to computer system 130, where it may be processed. In some embodiments, the processing may be carried out or facilitated by one or more software agents, as described herein. In some embodiments the processing functionality, performed on monitor 141 and/or computer system 130 includes pre-processing and/or signal conditioning, such as removing noise or erroneous information.

Example operating environment 101 further includes computer system 130, which may take the form of one or more servers (such as server 140 of FIG. 1A), and which is communicatively coupled through network 150 to EHR system 160, and storage 132.

Computer system 130, an embodiment of which is described in connection to FIG. 1A, may comprise one or more processors operable to receive instructions and process them accordingly, and may be embodied as a single computing device or multiple computing devices communicatively coupled to each other. In one embodiment, processing actions performed by system 130 are distributed among multiple locations such as one or more local clients and one or more remote servers, and may be distributed across the other components of example operating environment 101. For example, aspects of user/clinician interface 142 and/or software application 143 may operate on or utilize computer system 130. Similarly, a portion of computing system 130 may be embodied on user interface 142, application 143, and/or EHR system(s) 160. In one embodiment, system 130 comprises one or more computing devices, such as a server, desktop computer, laptop, or tablet, cloud-computing device or distributed computing architecture, a portable computing device such as a laptop, tablet, ultra-mobile P.C., or a mobile phone.

In some embodiments, computer system 130 is a computing system made up of one or more computing devices. In some embodiments, computer system 130 includes one or more software agents, and in an embodiment includes an adaptive multi-agent operating system (an example of operating system 129, described herein), but it will be appreciated that computer system 130 may also take the form of an adaptive single agent system or a non-agent system. Computer system 130 may be a distributed computing system, a data processing system, a centralized computing system, a single computer such as a desktop or laptop computer or a networked computing system.

Embodiments of computer system 130 may include computer software stack 121, which in some embodiments operates in the cloud, as a distributed system on a virtualization layer within computer system 130, and includes operating system 129. Operating system 129 may be implemented as a platform in the cloud, and which is capable of hosting a number of services such as 122, 123, 124, 126, 127, and 128. Some embodiments of operating system 129 comprise a distributed adaptive agent operating system. Embodiments of services 122 through 128 may run as a local services or may be distributed across one or more components of operating environment 101, in the cloud, on one or more personal computers or servers such as system 130, mobile device 120 (or a computing device supporting communications of RF beacon 180) and/or a computing device running interface 142 or application 143. In some embodiments, services 122 through 128 take the form of one or more software programs or routines, which may be employed by a software agent, and in some embodiments one or more of services 122 through 128 is embodied as a software agent. In some embodiments, interface 142 and/or application 143 operate in conjunction with software stack 121 and/or one or more services 122 through 128.

Authentication services 122 and access control permissions services 123 provide security and privacy related services for validating transactions with mobile device 120 including subscription requests, such as described in connection to subscription service 190 of FIG. 2A and step 350 of FIG. 3A. For example, in some embodiments services 122 and 124 facilitate validating credentials information. Information-set logic services 124 facilitates determining the set of information items, such as at step 320 of the method described in connection to FIG. 3A, including ranking and prioritizing the items. In some embodiments, services 124 also facilitates determining the subset of information items such as described at step 360 of the method in FIG. 3A. In some embodiments the services 124 operates in conjunction with message assembly services 126 for determining the subset of information items such as described at step 360. Message assembly services 126 facilitates the preparation or receipt of information communicated to or from mobile device 120, such as described in steps 310 and 360 of FIG. 3A and steps 311 and step 331 of FIG. 3B. Update subscription registry service 128 facilitates maintaining the registry of subscriptions such as described in connection to subscription service 190 in FIG. 2A. In some embodiments, subscription registry services are carried out my updates subscription service 190. Some embodiments of software stack 121 include software services 128, which may be embodied as an Apache Hadoop and Hbase framework, or similar frameworks operable for providing a distributed file system.

Some embodiments of stack 121 may further comprise services for utilizing an Apache Hadoop and Hbase framework (not shown), or similar frameworks operable for providing a distributed file system, and which in some embodiments facilitate provide access to cloud-based services such as those provided by Cerner Healthe Intent®. Additionally, some embodiments of stack 121 may further comprise one or more services stream processing service(s) (not shown). For example, such stream processing service(s) may be embodied using IBM InfoSphere stream processing platform, Twitter Storm stream processing, Ptolemy or Kepler stream processing software, or similar complex event processing (CEP) platforms, frameworks, or services, which may include the user of multiple such stream processing services (in parallel, serially, or operating independently). Some embodiments of the invention also may be used in conjunction with Cerner Millennium®, Cerner CareAware® (including CareAware iBus®), Cerner CareCompass®, or similar products and services.

Example operating environment 100 also includes storage 132 (or data store 132), an example embodiment of which is described in connection to FIG. 1A. In some embodiments, storage 132 includes patient data for a candidate or target patient (or information for multiple patients), including raw and processed patient data; variables associated with patient recommendations; recommendation knowledge base; recommendation rules; recommendations; recommendation update statistics; an operational data store, which stores events, frequent itemsets (such as "X often happens with Y", for example), and item sets index information; association rulebases; agent libraries, solvers and solver libraries, and other similar information including data and computer-usable instructions; patient-derived data; and health care provider information, for example. It is contemplated that the term data includes any information that can be stored in a computer-storage device or system, such as user-derived data, computer usable instructions, software applications, or other information. In some embodiments, data store 132 comprises the data store(s) associated with EHR system(s)

160. Further, although depicted as a single storage data store, data store 132 may comprise one or more data stores, or may be in the cloud.

FIG. 1C is provided as another aspect of an operating environment 102 suitable for practicing embodiments of the invention and includes many of the components described in connection with FIGS. 1A and 1B.

Figure 2A:
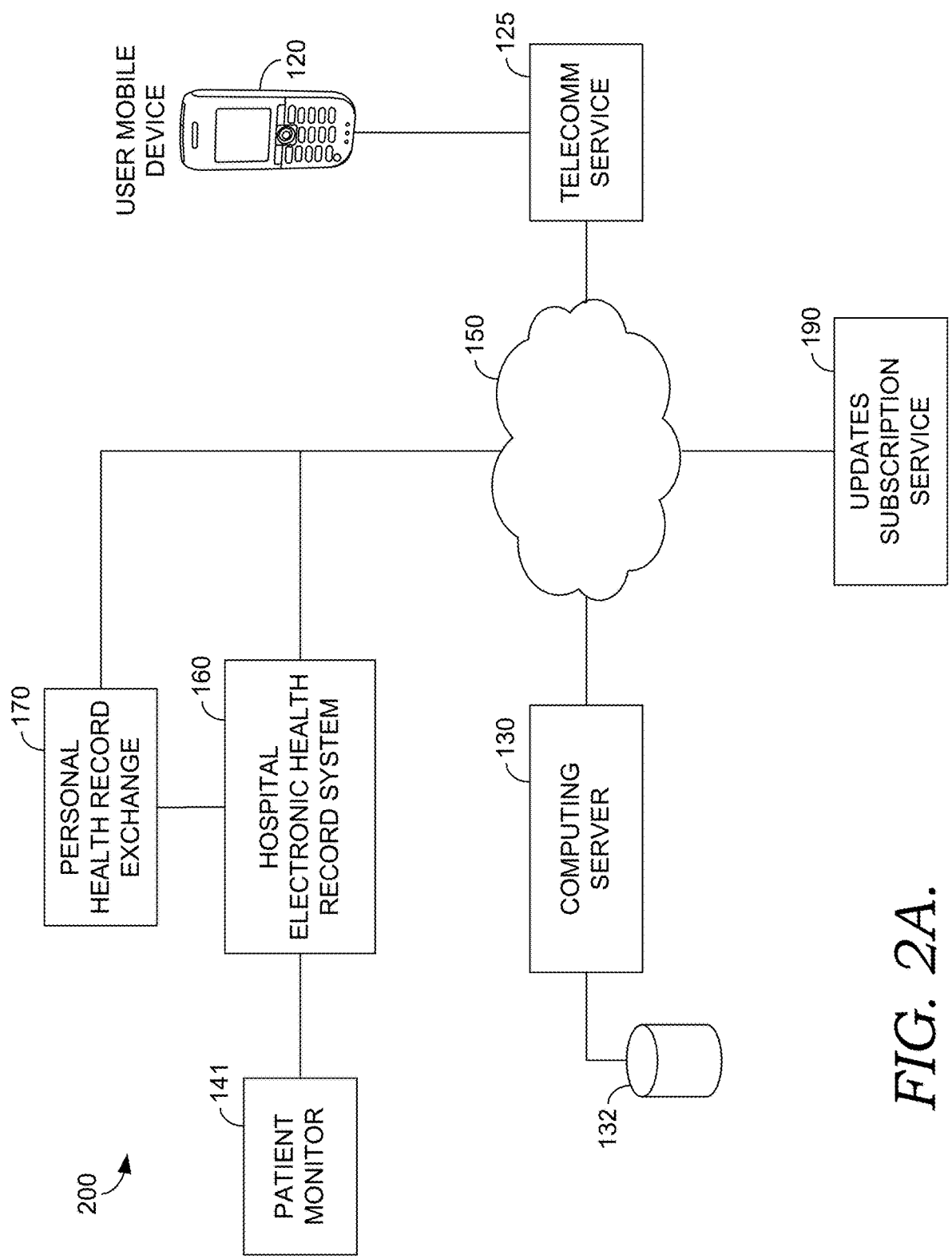
FIGS. 2A and 2B depict embodiments of the invention and aspects of an illustrative operating environment suitable for practicing embodiments of the disclosure also showing telecom or mobile data services.
Figure 2B:
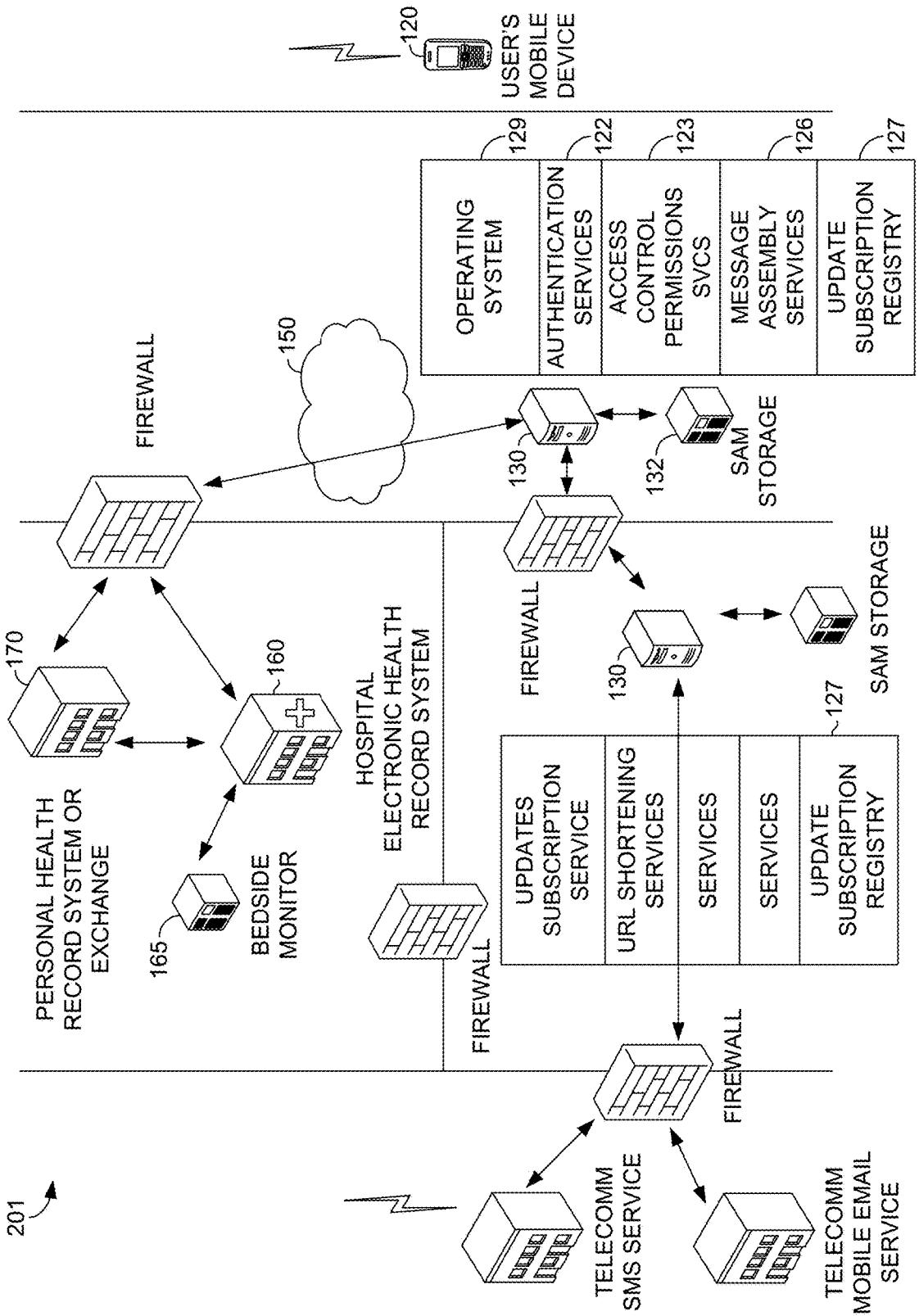

Turning now to FIGS. 2A and 2B, FIG. 2A depicts another exemplary operating environment 200 suitable for practicing an embodiment of the technologies described herein. In environment 200, mobile device 120 is communicatively coupled to telecom service 125. In some embodiments, telecom service 125 is provided by a mobile service provider such as AT&T, Sprint, or Verizon, for example, and includes mobile web or data service, mobile e-mail service, mobile SMS service, or a combination of these services. Environment 200 also includes updates subscription service 190. Subscription service 190 facilitates user-subscription functionality and in some embodiments includes an update subscription registry, which includes information specifying subscriptions and registers information updates for subscribed-to concepts, topics, groups of concepts, or information items. In one embodiment, the update subscription registry is used to determine which updates a user's mobile device should receive, based, in one embodiment, on information about available updates and, in one embodiment, also based on information about which updates the mobile device has already received.

In one embodiment, subscription service 190 receives information from mobile device 120 specifying information about the user's mobile device, bandwidth, data connection speed, user feedback, and other information in addition to information related to the reference pointer. Subscription service 190 uses this additional information for managing the communication of a subset of information items, from the set of information items identified by the reference pointer, to the mobile device, in one embodiment. For example, subscription service 190 may throttle the information or only provide the most important information items, where a mobile device's data connection is limited. In one embodiment, the communication is managed by computing system 130 or a server (not shown, such as server 140 or FIG. 1A), and in one embodiment, the information received from mobile device 120 is used to determine the priority or ranking of the information items in the set of information items, as further described below in connection to step 320 of FIG. 3A.

In some embodiments subscription service 190 receives a subset of information items related to those items subscripted to (or indicated by) a user, and facilitates the communication of the subset of information items to the mobile device. For example, subscription service 190 may prepare for sending via SMS, a message containing a secure hyperlink to the subset of information items, in an embodiment. In an embodiment, subscription service 190 functions as a server, such as server 140, and in one embodiment, subscription service 190 is part of server 140 or part of computing system 130. For example, in an embodiment subscription service 190 takes the form of one or more software programs or routines, or software agents residing on computing system 130.

In one embodiment, subscription service 190 receives requests from a mobile device for information associated with the reference pointer. In one embodiment, subscription service 190 manages the security and authentication of a user's mobile device when a request is received or before third-party information is provided to the mobile device. In some embodiments, subscriptions may expire. For example, a user may only be permitted to view data about a particular patient for a limited duration of time. Or after a period of time, information about a particular patient may no longer be useful (e.g., if the patient has recovered and is no longer being monitored.) It is contemplated that in such embodiments, subscription service 190 manages the subscription lifetimes, thereby facilitating individual subscriptions to expire or be renewed. In one embodiment, subscription service 190 throttles information provided to mobile device 120. In one embodiment, the throttling is intelligently determined using a rules engine or agent, such that only the most important information is updated as it becomes available, and less important information items are updated periodically, such as once every hour. In one embodiment, subscription service 190 throttles information so as to conserve bandwidth usage.

FIG. 2B provides as another example operating environment suitable for practicing embodiments of the technologies disclosed herein and includes many of the same components described in connection to FIGS. 1A-1D and 2A.

Figure 3A:
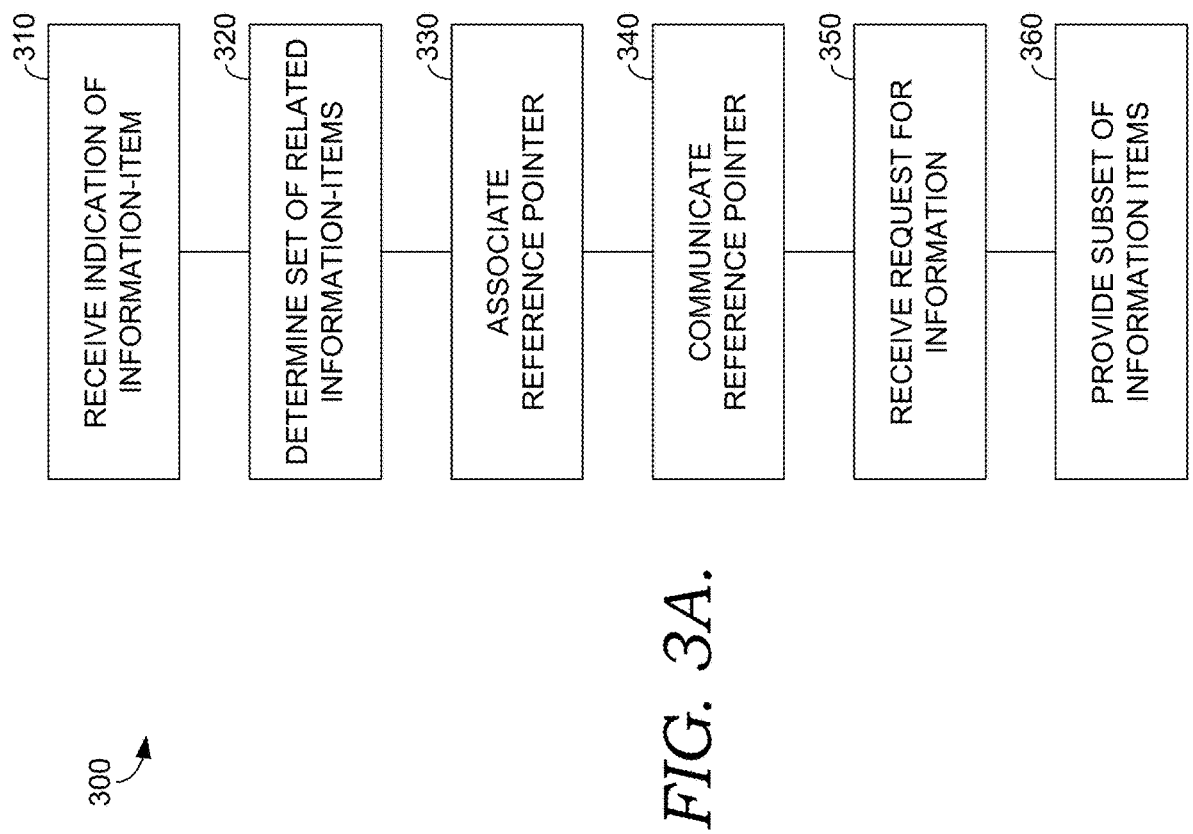
FIGS. 3A and 3B depict flow diagrams of exemplary methods for providing clinical decision support, in accordance with embodiments of this disclosure.

Turning now to FIG. 3A, a flow diagram 300 is provided illustrating, at a high level, an exemplary method according to one embodiment. Some embodiments of method 300 (and method 301, described in connection to FIG. 3B) may facilitate serially monitoring patients in health care clinics or at home or in other ambulatory or acute care settings by means of short-range radiofrequency beacons worn or carried by the patients and providing secure and timely updates regarding context-relevant, role- and venue-based electronic health information of said patients via the mobile devices of selected provider clinicians or other authorized caregivers who are responsible for the patients' care. At a step 310 an indication of one or more information items is received. The one or more information items may be received by way of clinician/user interface 142, mobile device 120, or a communication such as a request, received by mobile device 120 or computing system 130. In one embodiment, the information items include topics, concepts, or group of interrelated concepts associated with a third person, such as a patient. By way of example and not limitation, in one embodiment, while browsing in Electronic Health Records (EHR) or Patient Health Records (PHR), a clinician user or consumer user notices an information item of interest. Here, the information items might include, for example, patient-related item(s), about which the user wishes to receive automatic future updates; venue-related item(s), such having an Mpage for a particular unit delivered to the user until the user is no longer on-call; or role-related item(s), such as all cardiology consults until the user is off-service.

In one embodiment, information items are associated with one or more index codes, such as the Cerner Knowledge Index (CM), which identify or categorize information items as structured discrete data elements that can be represented by coded concepts within a data dictionary or an ontology. In one embodiment, a healthcare provider selects information items associated with a patient, and the items are received via a user interface, such as user interface 142. For example, turning briefly to FIGS. 4A and 4B, a healthcare provider might select (as indicated by the checked checkboxes) the Hypertension and Hyperglycemia information items. These selected items are then received via user interface 142. In one embodiment, an indication of one or more information items is received via a user interface 142 as a selection of items, from a user. In one embodiment, the user rubber-bands or groups a set of information items on the user interface 142, and then clicks a button or touches the screen to indicate that he or she wishes to subscribe to information related to that group of information items. In one embodiment, an indication of one or more information items is provided by an agent or recommendation engine, which may take the form of a request. In this embodiment, the indication might not be received by user interface 142, but instead received directly by computing system 130 or server 140.

In some embodiments, an indication of one or more information items is received through mobile device 120 by way of audio or visual information. For example, using mobile device 120 a user may speak a request for information items directed to mobile device. The mobile device then employs voice-recognition functionality to decode the words spoken in the user's request. In embodiments, the decoded words are then analyzed to determine the one or more information items. In another example, using a camera feature of mobile device 120, a user may capture an image which contains graphical information of the items of interest, such as a picture of a patient's chart. In some embodiments, the mobile device 120 may then employ object-character-recognition or patter recognition functionality to determine the information items from the captured image. While in some embodiments information representing the captured image is communicated to computing system 130 where character or pattern recognition is performed to determine information items. Additionally, in the example of receiving audio of visual information, some embodiments may employs a confirmation step allowing the user to confirm the information items before continuing.

At a step 320, a set of information items is determined such that members of the set of items are related to the information item for which an indication was received at step 310. For example, if the indication of an information item received in step 310 was for hypertension, then at step 320, a set of information items related to hypertension is determined; this set might include blood pressure, sodium levels, weight, and other information items related to hypertension. In one embodiment, information-set logic services 124 (described in FIGS. 1B and 1C) is used to determine the set of related items. Logic services 124 may further employ rule tables, a rules engine, or software agents. Thus in one embodiment, one or more agents determine the set of related information items; for example an agent may learn that a particular information item has significance for a patient with a given condition, and thus include that information item in the set of information items. In embodiments using index codes, such as CKIs, the CKIs corresponding to the indicated information items are first determined. Then, a set of information items is determined based on those CKIs.

In one embodiment, the set of related items is prioritized or is ranked according to criteria, such that a subset of information items, based on rank or priority, can be determined and communicated to a mobile device. In particular, in some situations, it is impractical to provide to the mobile device every information item in the set of information items. Not only is a smaller display screen on a mobile device less auditable for viewing large amounts of information, even if it were, the user may not want to sift through that much information. Some information items are less significant or meaningful or outdated, while other information items may be more relevant to determining a patient's condition. For example, if the third party is a patient who recently suffered a heart attack, then information items for blood-pressure and pulse carry more significance for this patient than if the patient were a teenager with a broken arm; accordingly blood pressure and pulse would likely be determined to have a higher priority for this patient, than if the patient were a teenager. Thus in some embodiments, it is desirable to rank or prioritize the information items, so as to maximize value to the user.

In some embodiments one or more criteria are used to perform the prioritization or ranking of the information items. Furthermore, in some embodiments, the ranking or prioritization may be determined by an agent, logic or rules engine, or by user preferences. For example, in one embodiment, a user or agent may designate a particular information item or class of information items as being more important. For example, if the user is a healthcare provider who is monitoring only patients who are pregnant, the user may always prefer to see the blood pressure (or the class of information items concerning blood, which could include blood pressure, pulse, various chemical-levels present in the blood, and other blood-related information items). In one embodiment, historical information, such as previous user actions, preferences, and user patterns—from a single user or multiple users—may be used as criteria for prioritization or ranking. For example, if users repeatedly associate a given information item with a patient having a certain condition, then over time, that item may be weighted as having a higher priority for patients with a similar or identical condition.

In one embodiment, the criteria include the age or staleness of a particular information item. For example, a user would be less interested in receiving an update of an information item that has not changed or is no longer relevant. (E.g., a user would probably not be interested in receiving updated information about a patient's pulse from three weeks ago.) Individual information items and classes of information items may have a temporal value associated with them, in some embodiments, which can indicate for how long the information is considered useful. In one embodiment, an agent or rules engine, using a rules table for example, determines the useful lifetime of a particular information item based on that item and the patient's condition. For example, a table may indicate that an information item for pulse when the third party patient is a teenager is only significant for 2-3 hours. Thus, this information item would have a higher priority (or better ranking) within the first 2-3 hours after the pulse was determined. Afterwards, its priority or ranking would diminish. Accordingly, as time passed beyond 2-3 hours, it would be increasingly less likely that the pulse information item would be communicated to the mobile device because its priority (or ranking) would be lower. This is different from the temporal aspect of the user's subscription, discussed below, which contemplates that a user may only desire to know about or be permitted to access information about a third-party patient for a given amount of time or that a user's access may be temporary. In these cases, the user's subscription to a set of information items may expire after a period of time.

In some embodiments, the criteria include a third party's condition. For example, where the third party is a patient who just suffered a heart attack, information items related to the heart might be determined to have a higher priority (better ranking) than those information items would have, if the patient were a teenager with a broken arm. In some embodiments, the criteria include information about the group of items that the user selected or were indicated in step 310.

In some embodiments, the criteria include information about the number of third parties that a user is subscribed to or is receiving updates for. In these embodiments, which are described below in connection to step 360, care is taken not to flood the user with excess information, thereby diminishing the value of providing the user with updated information on a mobile device. In one embodiment, the criteria include the significance of change in a particular information item or group of information items. For example, a minor change in heart rate of 3 to 4 beats per minute is less significant than a major drop in blood glucose levels. Thus, an updated information item that indicates a change in heart rate of +3 beats per minute would have a lower priority (worse ranking), than an updated information item indicating a major change in blood glucose levels of +200 MG/DL. In some embodiments as described herein, the criteria include spatial proximity of the third party (e.g., patient) to the user, which may be determined based on the user's mobile device (or similar wireless-communications enabled computing device) detecting a beacon communication from an RF beacon 180.

Continuing with FIG. 3A, at a step 330, a reference pointer is associated with the set of related information items. In an embodiment, the reference pointer is an address, such as a URL, physical address, logical address, or mapping to a location in information store 132 that stores the set of related information items. In an embodiment, the reference pointer comprises information usable by computing system 130 to determine the one or more information items provided by in step 310. In an embodiment, a reference pointer is a set of pointers or addresses to all of the individual pieces of information items in the set. In an embodiment, a reference pointer is a code that is associated with an identifier, such as a physical address, or logical address, or table of addresses, that identify the set of related information items. For example, in this embodiment, a table or database may be associated with the reference pointer (here a code), thereby mapping the reference pointer to the set of information items. One advantage of having a reference pointer as a code and not an actual physical or logical address is that the code can always be the same length. Additionally, the code might be rendered meaningless without the associated identifier; thus, security advantages are provided because the reference-pointer code can be communicated without identifying any information about the set of information items that are associated with the reference pointer. Thus, for example in one embodiment a pseudorandom code can be generated, using computing system 130, and used as reference pointer by associating it with a set of information items. Moreover, the association between the code and the set of information items is made secure so that only a user with authorized credentials can access information in the set of information items. An unauthorized user might not be permitted to see or detect the association, let alone the set of information items.

At a step 340, the reference pointer is communicated to a mobile device. In one embodiment, the reference pointer is sent via SMS text message or e-mail to the mobile device. In one embodiment, the reference pointer is communicated over Bluetooth, Wi-Fi, or other wireless-communication technologies. For example, as described herein, the reference pointer may be communicated via a wireless-communication beacon such as RF beacon 180. In an embodiment, the reference pointer is encoded in a communication emitted from RF beacon 180. For instance, the reference pointer may be communicated over Bluetooth Low Energy (BLE, such as Bluetooth 4.0) or other short-range wireless-communication technologies, in an embodiment. In one embodiment, the reference pointer is communicated to the mobile device as an update within an app. For example, an app running on the mobile device might include functionality as described above for identifying RF beacon emissions and receiving the reference pointer.

In embodiments, the reference pointer is encoded within a BLE beacon as any one or more of a UUID, a major number code, and a minor number code, and associated tag attribute codes, any one or more of which may be stored within the beacon device's memory (e.g., flash memory). In embodiments, the organization and service are encoded in the UUID and a patient identifier is encrypted in the 16-bit Major number and/or the 16-bit Minor number. In embodiments, any one or more related context identifiers may be encrypted in the 16-bit Minor number, local memory on the beacon device (e.g., flash memory), and/or mass storage memory on the EHR system. In an embodiment where one or more related context identifiers is encrypted in the mass storage memory on the EHR system, the one or more related context identifiers may be retrieved by a mobile application, suitably authorized in accordance with aspects discussed herein. In one embodiment, the reference pointer may comprise an address corresponding to the set of information items or an index code that identifies or categorizes the set of information items as structured discrete data elements, either of which is usable for identifying the set of information items. Further embodiments of information items and index codes are discussed above in connection to step 310 of FIG. 3A. In an embodiment, the reference point may expire after a certain amount of time, which may have the effect of revoking access to the set of the information items.

At a step 350, a request is received for information from the set of information associated with the reference pointer. In one embodiment, mobile device 120, having received the reference pointer, now requests information pointed to by the reference pointer. The request is received by server 140, subscription service 190, or a server operating on computing system 130, in an embodiment. For example, in one embodiment, if a user has subscribed to heart-related information about a particular patient, the user's mobile device 120 (having received the reference pointer, which points to information from the set of heart-related information determined in step 320) now communicates a request for information that is associated with the reference pointer. In one embodiment, mobile device 120 communicates the reference pointer, or information associated with the reference pointer such as a portion of the reference pointer code, to server 140 or subscription service 190.

In one embodiment, mobile device 120 may also communicate credentials or authorization information. In some embodiments, credentials or authorization information includes user credentials, subscription credentials, or both. In one embodiment, user credentials identify the user, which can be used to determine which information or which types of information a user is permitted to access. In one embodiment, user credentials do not identify the user, but specify the information or types of information that a user is permitted to access. Subscription credentials specify information about the user's subscription, which in one embodiment, can be discretized to a per-patient or per-information item level. In one embodiment, subscription credentials include authorization information from the third party for which the information is concerning. In one embodiment, subscription credentials specify how long a particular information item or set or subset of information items, can be accessed. For example, if a user is authorized to access data for a patient only for a specified period of time, then after the credential expires, the user will no longer be permitted to access updated information for that patient. In one embodiment, a user may only desire to know about a third-party patient for a given amount of time. In the proceeding embodiments, the user's subscription to a set of information items or a particular information item may expire after a period of time. In one embodiment, the mobile device will no longer request information after the subscription has expired. In one embodiment, the mobile device will display an indication to the user that the user's credential has expired or that the user is not permitted to access the information requested.

In some embodiments, computer system 130 or server 140 may include a service such as access control permissions services 123 for authenticating a user as a medical provider authorized to receive the medical data based on a location of the user near at least one beacon located in association with a patient for which the medical data is provided. The patient and beacon can be located in a room within a hospital, medical facility, medical clinic, etc. The mobile device 120 (or computer system with wireless communications that detects the beacon) enables the medical provider to obtain the relevant information about the patient, and related information including receiving treatment checklists, obtain treatment guidance, recording a medical procedure as video via a camera (e.g., video camera) integrated with the mobile device 120 and make medical annotations while treating the patient. The annotations and video can be securely stored in the patient's EHR 160 or in a server (e.g., server 140 or computer system 130) as a medical record in association with the patient and made available for subsequent retrieval by authorized medical providers. Checklists and health guidance can also be obtained from the server. Note that in an embodiment, a step or logical operation can be provided for authenticating an identify of the healthcare provider prior to authorizing access to the healthcare records. In an embodiment, authentication for access may comprise: at least one of acquiring a biometric; and acquiring entry of a passcode from the healthcare provider; and an RFID tag and/or NFC-enabled credentialed smartcard or worn bracelet that is challenged throughout a healthcare facility (e.g., upon entry into a patient's room, wherein a patient awaits treatment).

In one embodiment, the healthcare provider can revoke or grant credentials at any time. For example, in one embodiment, the healthcare provider maintains a database, which takes the form of a relational database of credential information associated with users, patients, or concepts. Using this database, the healthcare provider can alter credentials associated with a patient, user, or concept, at any time. Thus, the information that a user is permitted to access can be controlled dynamically by the healthcare provider. By way of example, if the healthcare provider determined that a particular user is no longer permitted to have access to information about a particular patient, then the credential information in the database that is associated with that user and that patient would be set so as to prevent access to the patient information, thereby effectively revoking credentials, in one embodiment.

In one embodiment, a third party, such as a patient, is permitted to provide input for determining credentials. For example, a patient might set access-permission levels; in one embodiment, the patient might do this by logging on to a secure website maintained by the healthcare provider. In one embodiment, the third party may identify particular information items for which they desire to block access. In one embodiment, the third party might consent, or provide permission, to allowing information items to be made accessible to a user, such as their doctor, using the technologies of the present invention. In one embodiment, the third party provides the consent by logging on to the secure website. In embodiments such as these, the third party is provided control over what information is made accessible, to whom it is accessible, and for how long it is accessible.

In some embodiments, a user may only desire to know about a third-party patient (or similar target) when the user is in spatial proximity to the third party patient. In the proceeding embodiments, the user's subscription to a set of information items or a particular information item may expire once the user is no longer in spatial proximity, such as when the user's mobile device 120 no longer detects communication from an RF beacon 180. In one embodiment, the mobile device will no longer request information after the subscription has expired.

Some embodiments described herein may be configured to monitor beacons and respond, such as by communicating a callback when a user mobile device is sufficiently close to one or more beacons and, in some instances, when corresponding proximity rules are triggered. As described above, beacons may emit or broadcast information continuously, periodically or in response to a ping or hail from a detecting device. Certain hardware beacons, such as iBeacons are Bluetooth Low Energy devices which keep emitting their identity at a predefined frequency (e.g., every 500 milliseconds), this broadcasting is also known as advertising interval. These signals are emitted at a fixed transmission power which is usually measured in dBm (dB-milliWatt). Typical values are −4 dBm, −8 dBm, −16 dBm. These signals can be detected by mobile device at distances up to approximately 70 m.

In a typical deployment scenario where multiple beacons might be deployed as close as 50 centimeters from each other, a mobile device would receive signals from more than one beacon at a time. All the beacons may be configured to have the same UUID which is common to the organization. However, each one may be configured to have a different identity as defined by two other numeric codes (Major and Minor) plus, optionally, additional tags. UUID: 16-byte number typically common across an organization, e.g., Major: 2-byte number (0 to 65,535), Minor: 2-byte number (0 to 65,535). In the embodiments described herein that use tags: a list or vector of 4-byte numbers (0 to 4,294,967,295) may be used with each vector element denoting a concept or attribute or property or an entity with which the beacon-bearer has a relationship. In these embodiments, the combination of UUID, Major, and Minor may be unique, thereby making each beacon readily identifiable from other beacons.

In one embodiment, each subscription or requested information item has a subscription ID or information item ID that is also received at step 350. In one embodiment, the ID includes information about the time that the last update for that subscription or information item was received. Alternatively, the received request can include information specifying when a particular update was last received. In these embodiments, server 140, subscription service 190, or other software services, routines, or agents operating on computing system 130 may determine the time duration since the last update was received and/or which update was last provided to the mobile device. Accordingly, by receiving information about which updates or subscriptions are on the mobile device, server 140 or subscription service 190 can determine which updated information should be provided to the user. Moreover, in some embodiments, the received information about which updates or subscriptions are on the mobile device is used as criteria for prioritizing (or ranking) information items to be provided to the mobile device. For example, suppose that subscription service 190 received information indicating that the last blood-pressure-related information on a mobile device is from over 48 hours ago, then this information may be used to assign a higher priority (or better ranking) to blood-pressure-related information, thereby increasing the likelihood that blood-pressure-related information will be provided in the next update of information sent to the mobile device.

In one embodiment, the received request for information of step 350 may be accompanied by other information, such as for example, information about the mobile device sending the request such as its location, the mobile service provider (e.g., AT&T, Verizon, or Sprint), the mobile device's signal strength, or the number of subscriptions to which the user is subscribed. In these embodiments, this information may be used as criteria for prioritizing the set of related information items, or may be used to control which information items are communicated to the mobile device, as described next in step 360, and when those information items are communicated to the mobile device. For example, in situations where the mobile device has diminished signal strength, is roaming, or has a smaller-bandwidth connection such as a 3G connection, it may be advantageous, in some embodiments, to provide fewer information items to the mobile device, or throttle the communication of information items to the mobile device. Thus, only higher priority or ranked information items, or information items determined to be critical or urgent, would be communicated to the mobile device, in these embodiments. Similarly, in situations where the mobile device is in spatial proximity to multiple RF beacons 180, information items corresponding to those patients or targets that are nearer to the user may be prioritized or ranked higher. Nearness may be determined, by way of example and not limitation, based on signal strength of the RF beacon and/or by comparing the location of the mobile device 120 and a known location of the RF beacon 180 (such as a particular patient bed or hospital floor). In this way, a user moving through a hospital (or any setting with multiple RF beacons 180) may only see information for those targets closest to the user.

At a step 360, a subset of information items from the set of information items is provided to the mobile device. In one embodiment, the subset of information items includes the higher priority or ranked information items. Thus for example, where the set of information items determined in step 320 includes hundreds of items, which have been prioritized or ranked, at step 360 a subset of this set, comprising the items having a higher rank or priority, is provided to the mobile device, in this embodiment. In some embodiments, the subset of information items is provided using either "push" or "pull" technologies. For example, in one embodiment, the subset is provided as a "push" of information by way of a data connection. In another embodiment, the mobile device "pulls" the subset of information items. In one embodiment, the mobile device receives a notification that updated information is available, and an app running on the mobile device initiates a communication session to receive the subset of information items.

In one embodiment, the determination of which information items are included in the subset is determined by criteria such as the criteria used to rank or prioritize the user preferences. For example, in one embodiment, only urgent or the most highly ranked or prioritized information items are provided to the mobile device as they become available. Other information items (i.e., those not having high priority) may be provided periodically, such as once every several hours. In some embodiments, the communication of subset of information items to the mobile device is throttled. In one embodiment, certain information items may not be provided at all, based on the criteria. For example, suppose a user has subscribed to blood-related information about a particular third party. Thus, in step 310, an indication of blood-related information items were received, and at step 320, the set of all information items related to blood for that patient was determined. Suppose that one blood-related information item in the set is information specifying that the patient's blood type is A+. This information may have little value to a user who is using her mobile device to conveniently monitor a patient's status using the technologies of our invention. (In some embodiments, a software agent or rules engine might determine that blood-type is of little relevance given the patient's condition or historical user information. In some embodiments, the user may have indicated, through a user-preferences setting, that the user doesn't want to see blood-type information.) Thus the patient's blood type will likely be determined to have a lower priority, in embodiments that prioritize the information items. Accordingly, it is possible that the information item about a patient's blood type is not provided to the mobile device as part of the subset provided in step 360.

In some embodiments, the criteria include information about the number of third parties that a user is subscribed to or receiving updates for. In these embodiments, care is taken not to flood the user with excess information, thereby diminishing the value of providing the user with updated information on a mobile device. Thus for a user who is receiving information related to multiple patients, only the most important information for each patient may be provided; but where a user has only one patient, then more information items may be provided. It is further contemplated that in some embodiments communication of information is done securely so as to minimize the possibility of information theft and comply with HIPPA requirements. For example, the reference pointers or communicated information may be encoded and/or require credentials, as described herein.

In some embodiments, before or after the subset of information items is provided, a user is able to request additional information about a patient, such as by using his or her mobile device 120. For example, in some embodiments, an app (such as application 143, described in FIG. 1B) running on the mobile device may present to the user a button or option to "show more" information about the third party that the user is monitoring. In some embodiments, the user is provided a means to provide feedback based on the subset of information items received. For example, in one embodiment, the user can place orders or add comments or notes into the mobile device, via an app running on the mobile device. Such feedback may be securely communicated to server 140, in one embodiment.

It should be appreciated that some embodiments described herein benefit a user by providing access to other records associated with a patient. Embodiments may enable health care professionals to access a patient's medical treatment records; however, a primary care physician (PCP) with long-term patient relationship may benefit from having access to a patient's health maintenance records (e.g., records associated with fitness, diet, physical therapy, etc.) as well as educational records, or other records. For example, a patient's school records from K-12 may provide additional insight to a therapist working with the emotional or psychiatric needs of the patient. There may be information (e.g., discipline, grade reports, etc.) that can be helpful in identifying the trigger for a patient's state of mental health. Record form additional training and education may also be considered useful. Similarly, records from employees, military, etc. could offer similar insight and benefits to a treating physician or caregiver.

In some embodiments, a confirmation that the subset of information was delivered to the mobile device, occurs. For example, in one embodiment, mobile device 120 sends an indication of receipt of the subset of information to subscription service 190 or server 140. In one embodiment, this receipt is further used to determine which updates to provide to a particular user's mobile device, based on which updates have already been received, and in one embodiment the receipt is used as criteria for ranking or prioritizing the information items in the set of information items. For example, if a mobile device was unable to receive updates for a period of time, such as 18 hours, then a particular information item, such as a patient's pulse from 17 hours ago, may no longer be included in the subset of information items communicated to the mobile device because it is less significant or useful to the user (i.e., it has dropped in ranking or priority). Whereas, if that particular information item would have been included for an update received 16 hours ago, it would no longer be included in the next update communicated to the mobile device.

As described above, some embodiments may utilize triggering rules and corresponding actions for detecting a beacon and/or receiving specific information from a patient identified form a reference pointer communicated from a beacon. A triggering rule may comprise a combination of multiple conditions, the primary condition being proximity to a beacon. Other conditions may include time spent near the particular beacon or other user attributes configurable via custom attributes as described herein. In one embodiment, an example rule may comprise: IF (the clinician's mobile device 120 running an app 143 to detect an RF beacon 180) has camped onto RF Beacon 180 with Major:231 Minor: 4328 (beacon identification) AND the clinician user has spent more than <30> seconds in the proximity of this beacon AND the clinician user is a provider of care services for the <St. John Depression Group Therapy> group AND the beacon bearer (i.e., the target patient) is <female> AND the beacon bearer has an active diagnosis of <bipolar depression> AND a beacon tag denotes that the beacon bearer is a member of the <St. John Depression Group Therapy>group AND the group has a scheduled meeting <today> AND the date is between the <1st and 31st of January> AND there are simultaneously <two> or more additional Beacons present whose bearers are members of the <St. John Depression Group Therapy>group), THEN (send a callback to the clinician mobile device app 143 with a reference to the Rule name, AND send a callback with a reference pointer to the tagged therapy group AND send information pertaining to the user plus other actions for the identified group as configured by the manager of an administration console).

In some embodiments, rules may have corresponding actions that may be executed. In the example reduction-to-practice described below, five types of actions were configured from the communications service: Text Alert, Webpage, Cards, Webhook and Custom. Text Alert: This is the basic action type, which shows a popup alert on the user mobile device with a text message when the rule is triggered; Webpage: This directs the app by referencing an internet URL and the corresponding ASP or RESTful webpage is opened; Cards: This directs the app to render full-screen content appropriate to the context, configurable from the Admin Console; Webhook: This makes calls to EHR services with given JSON payload; and Custom: This allows one to add fixed JSON payload from the Admin Console. When the rule is triggered, the payload is passed from the communications service to the app, which can parse it and execute other tasks or methods.

In some embodiments, variations of method 300 (and method 301, described in connection to FIG. 3B) comprise (a) detecting the proximity of a target patient or patients to a responsible clinician user or other authorized caregiver user via reception, on the user-clinician's mobile device 120, of periodic RF transmissions emitted by an RF beacon 180 device of the beacon-bearing target patient; (b) determining relevant healthcare contexts that are applicable to the target patient or patients at that time; and (c) retrieving, updating, and presenting relevant electronic health record information (such as described in method 300) pertaining to the patient to the authorized clinician or caregiver user via an application 143 running on the user's mobile device 120.

Figure 3B:
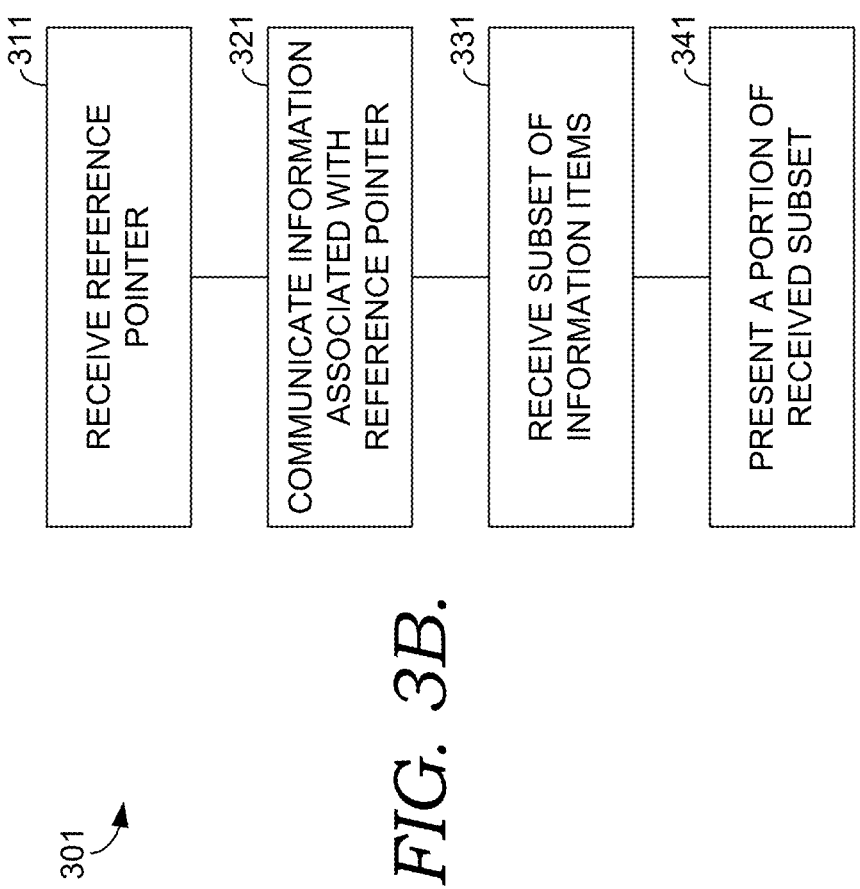

FIG. 3B depicts a flow diagram illustrating, at a high level, an exemplary method according to one embodiment and is shown as 301. At a step 311 a reference pointer is received by a mobile device. In one embodiment, the reference pointer is an address, such as a URL, physical address, logical address, or mapping to a location in information store 132 that stores a set of information items related to information items, which may also include topics, concepts, or groups of concepts, that a user or agent has selected or indicated. In one embodiment, a reference pointer is a set of pointers or addresses to all of the individual pieces of information items in the set. In one embodiment, a reference pointer is a code that is associated with an identifier, such as a physical address, or logical address, or table of addresses that identify the set of related information items. Further embodiments of a reference pointer are discussed above in connection to step 330 of FIG. 3A.

In one embodiment, the reference pointer is received by mobile device 120 at step 311 via SMS text message or e-mail to mobile device 120. In one embodiment, the reference pointer is communicated over Bluetooth, Wi-Fi, or other wireless-communication technologies and may be communicated via an RF beacon 180 or similar wireless communication-enabled device. In one embodiment, the reference pointer is communicated to mobile device 120 as an update within an app. For example, an app running on mobile device 120 might include functionality for receiving the reference pointer. In one embodiment, the reference pointer is encoded within a composite reference pointer or code, and communicated to mobile device 120 by way of capturing a representation of the reference pointer using mobile device 120. For example, computing system 130 might encode the reference pointer as a UUID plus BLE (or similar wireless communication format or other short-range RF protocol) major and minor codes plus associated codes, or similar encoding that references an itemset comprised of clinical and/or administrative items. Further embodiments of communicating and receiving a reference pointer are discussed above in connection to step 340 of FIG. 3A.

At a step 321, information associated with the reference pointer is communicated to server 140, subscription service 190, or a server operating on computing system 130. In one embodiment, the communicated information includes a request for receiving information from the set of information associated with the reference pointer. In one embodiment, the mobile device, having received the reference pointer, now requests information pointed to by the reference pointer. The request is received by server 140, subscription service 190, or by a server operating on computing system 130, in an embodiment. For example, in one embodiment, if a user has subscribed to heart-related information about a particular patient, the user's mobile device (having received the reference pointer in step 311), communicates a request for information that is associated with the reference pointer. In one embodiment, the mobile device communicates the reference pointer, or information associated with the reference pointer such as a portion of the reference pointer code, to server 140 or subscription service 190.

In one embodiment, the mobile device may also communicate credential information. In some embodiments, credential information includes user credentials, subscription credentials, or both. The embodiments of using credential information described above in connection to step 350 of FIG. 3A, are also applicable to some embodiments of step 321.

In an embodiment, the information communicated in step 321 includes a subscription ID or information item ID. In one embodiment the ID includes information about the time that the last update for that subscription or information item was received by the mobile device. Alternatively, the information communicated in step 321 can include information specifying when a particular update was last received. In these embodiments, server 140, subscription service 190, or computing system 130 is capable of determining how long it has been since the last update was received and/or which update was last provided to the mobile device. Accordingly, by receiving information about which updates or subscriptions are on the mobile device, server 140 or subscription service 190 can determine which updated information should be provided to the mobile device. Moreover, in some embodiments, the received information about which updates or subscriptions are on the mobile device is used as criteria for prioritizing (or ranking) information items to be provided to the mobile device. For example, suppose that subscription service received information indicating that the last blood-pressure-related information on a mobile device is from over 48 hours ago, then this information may be used to assign a higher priority (or better ranking) to blood-pressure-related information, thereby increasing the likelihood that blood-pressure related information will be provided in the next update of information sent to the mobile device.

In one embodiment, the information communicated in step 321 may be accompanied by other information, such as for example, information about the mobile device sending the request, the mobile service provider (e.g., AT&T, Verizon, or Sprint), the mobile device's signal strength, or the number of subscriptions to which the user is subscribed. In these embodiments, this information may be used as criteria for prioritizing the set of related information items, or may be used to control which information items are communicated to the mobile device, and when those information items are communicated to the mobile device. For example, in situations where the mobile device has diminished signal strength, is roaming, or has a smaller-bandwidth connection such as a 3G connection, it may be advantageous, in some embodiments, to provide fewer information items to the mobile device, or throttle the communication of information items to the mobile device. Thus, only higher priority or ranked information items, or information items determined to be critical or urgent, would be communicated to the mobile device, in these embodiments.

At a step 331, a subset of information items from the set of information items associated with the reference pointer, is received by mobile device 120. In one embodiment, the subset of information items includes the higher priority or ranked information items. Thus, for example, where a set of information items, which may be determined as described above in step 320 of FIG. 3A, includes hundreds of items, which have been prioritized or ranked, at step 331 a subset of this set, comprising the items having a higher rank or priority, are received by the mobile device, in one embodiment. In some embodiments, the subset of information items is received using either "push" or "pull" technologies. For example, in one embodiment, the subset of information is "pushed" to mobile device 120 via telecom service 125, server 140 or subscription service 190. In another embodiment, the mobile device "pulls" the subset of information items from server 140 or subscription service 190. In one embodiment, mobile device 120 receives a notification that updated information is available, and an app running on mobile device 120 initiates a communication session to receive the subset of information items.

In one embodiment, a determination of which information items are to be included in the subset is determined by criteria such as the criteria used to rank or prioritize the user preferences. For example, in one embodiment, only urgent or the most highly ranked (or prioritized) information items are provided to (and subsequently received by) the mobile device as they become available. Other information items (i.e., those not having high priority) are provided periodically, such as once every several hours. In some embodiments, communication of the subset of information items to the mobile device is throttled. In one embodiment, certain information items may not be provided at all, based on the criteria, as described in connection to step 360 of FIG. 3A.

In some embodiments, the criteria include information about the number of third parties that a user is subscribed to or is receiving updates for. In these embodiments, care is taken not to flood the user with excess information, thereby diminishing the value of providing the user with updated information on a mobile device. Thus, for example, a user who is receiving subsets of information for multiple third-party patients, only the most important information for each patient may be provided, or information from patient's in closer spatial proximity to the user may be prioritized, as described herein; but where a user has only one patient, then more information items may be provided, and subsequently received at step 331.

At a step 341, a portion of the received information is presented on the mobile device. An illustrative example of presenting a portion of a received subset is provided in FIG. 5, which shows information about a third-party patient. In one embodiment, only a portion of the received subset of information is presented because the mobile device 120 may have limited screen size, or a user may only care to see a portion of the information at a time. In some embodiments, the user can scroll, browse, or search through the remaining information in the received subset of information. In one embodiment, the information is presented on a graphical user interface, as is provided in the illustrative example of FIG. 5. In one embodiment, the information is presented as text, such as in an e-mail message or text message. For example, the received subset of information may be in the form of a text message, and the portion of the subset presented comprises the text of the text message, which might say, "Patient Jane Doe: BP 140/80; Pulse 60 BPM; Blood Glu 400 MG/DL . . . " for example. In one embodiment, the presented information includes a time-stamp indicating the age or staleness of the information. For example "BP 140/80 (10:43 AM CST); Glu 400 MG/DL (8:05 AM CST); . . . ."

Turning now to FIGS. 4A and 4B, illustrative examples of user/clinician interface 142, operating on different types of computer devices, are provided and referenced generally as 401 and 402, respectively. In particular, FIG. 4A depicts an embodiment of a smartphone-based (or mobile device 120 based) application 143 with display showing a graphical user interface 142. In one embodiment, the application 143 may comprise a representation of an electronic chart. In an embodiment, the application 143 may summarize and present relevant information to the user via notifications, update feed, or any other means of providing relevant information to the user without necessitating the opening of an electronic chart viewing application or an electronic chart itself. In one embodiment the application 143 on the mobile device is implemented as a SMART or FHIR application to facilitate interoperability among different electronic health record systems, insurer or health plan systems, pharmaceutical manufacturer and patient assistance systems, clinical trial data management systems, registry systems, or other health related information systems, such as public health information systems. FIG. 4B shows an example embodiment as a display on a wireless-communication-enabled PC computing device, such as computing system 130. In one embodiment, the user interface of FIG. 4B includes a touch screen, and in one embodiment, user interface of 4B includes other input means such as a keyboard, mouse, pad, voice-recognition module, or other means for receiving, from a user, an indication of information items. For example, in one embodiment, a user "checks" a checkbox adjacent to the information items for which he or she is interested in receiving updated information. In another embodiment, a user draws a box or loop around the information items of interest. In another embodiment, the user otherwise selects or provides an indication of information items of interest.

More specifically, in these illustrative examples, each of 401 and 402 depict a user interface presenting information about a third-party patient named Jane Mary Doe. Each of 401 and 402 has a user interface 142. In these embodiments of user interface 142, a user, such as a clinician or healthcare provider, can select those information items for which the user desires to receive updated information. The user is thereby subscribing to information related to the selected information items, here "Hypertension" and "Hyperglycemia." In one embodiment (not shown), the user may draw, with a finger, stylus, mouse, or similar input device, a circle or box around those information items for which the user wishes to subscribe, rather than selecting individual items. Following the receipt or a user's selection of information items, or after an indication of information items is received by a user or agent, an RF beacon 180 corresponding to the patient may be used to communicate an encoded reference pointer, which points to a set of information items related to the selected information items, in one embodiment.

Figure 5:
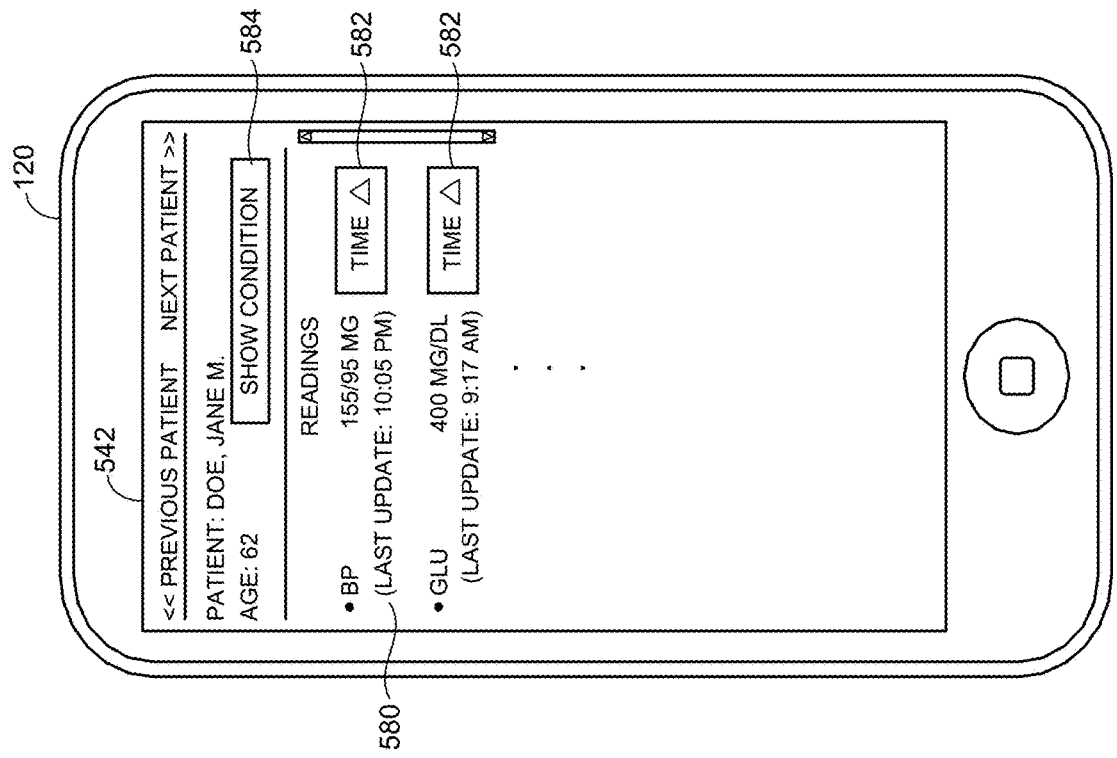
FIG. 5 depicts an example of a mobile device suitable for use in embodiments of the disclosure.

FIG. 5 illustratively shows an embodiment of mobile device 120. In the embodiment of FIG. 5, mobile device 120 includes a user interface 542, which may be a graphical user interface that is presenting a portion of a subset of information from a set of information related to one or more information items to which the user has selected or indicated. Thus, user interface 542 may be embodied as clinician/user interface 142 of FIG. 1B. In one embodiment, the subset of information presented with user interface 542 is facilitated by way of an app (such as application 143 of FIG. 1B) running on the mobile device 120. In the example depicted in FIGS. 4A and 4B, a user has subscribed to information relating to hypertension and hyperglycemia. User interface 542 depicts an example portion of a subset of information for which this user might be presented, with these subscriptions. Here, the subset of information includes information about blood pressure and blood glucose levels.

In one embodiment, the app facilitates user authentication, subscription credentials and security. For example, the app communicates credential information to server 140 or subscription service 190 when requesting information associated with the reference pointer. In one embodiment, the app receives and validates user authentication, such as a password, voice-pattern recognition, or pictogram entered by the user, via mobile device 120, or finger-print or eye-scan using a camera on mobile device 120. This prevents an unauthorized possessor of the mobile device from accessing or viewing confidential third-party information, should the mobile device 120 be stolen or used without permission. In one embodiment, mobile device 120 receives updates of information from the subset of information as the information becomes available or as it is communicated from subscription service 190 or server 140, but the app prevents a user from viewing the updated information until user authentication is received.

In one embodiment, user interface 542 also presents to the user information about the timeliness of the information item, if available. For example, in the embodiment shown in FIG. 5, item 580 shows a "Last Update: 10:05 p.m." adjacent to the information item for blood pressure. In one embodiment (not shown) user interface 542 also presents information about the time that the last update of information was received. In one embodiment, the mobile device maintains access to information about previously received updates, thereby allowing a user to view the changes in levels of a particular information item over time. For example, in the embodiment shown in FIG. 5, user interface 542 includes a "Time A" button such as Time-delta hotspot 582, adjacent to some of the information items, which when selected, touched, or pressed, enable a user to view the historical information about that information item. In one embodiment. For example, for the information item "BP" the user may see a chart listing Jane Doe's blood pressure for each of the previous updates received by the mobile device. In one embodiment, the previous update levels are presented as a graph, thereby enabling the user to more easily and quickly visualize changes in a patient's condition over time.

In some embodiments, user interface 542 contains functionality for receiving input from a user requesting additional information. For example, in the embodiment shown in FIG. 5, user interface 542 includes show-condition hotspot 584, which when selected, touched, or pressed, directs an app running on the mobile device to provide additional information about the patient's condition to the user via user interface 542. In one embodiment, the additional information includes information that is part of the subset of information already received on mobile device 120. In one embodiment, the additional information is requested from server 140 or subscription service 190.

In some embodiments, an app (such as application 143 of FIG. 1B) running on the mobile device 120 may present to the user a button or option to "show more" information about the third party that the user is monitoring. In some embodiments, the user is provided a means to provide feedback based on the subset of information items received. For example, in one embodiment, the user can place orders or add comments or notes into the mobile device, via an app running on the mobile device 120. Such feedback may be securely communicated to server 140, in one embodiment.

Example Reduction to Practice

Example 1

Single-beacon individual care context. In a first example reduction to practice, RF beacon 180 included a Texas Instruments CC2541F256 BLE chip comprising a 2.4 GHz radio with serpentine antenna on the 28 mm diameter printed circuit board. This CC2541 chip has a 32-bit ARM® Cortex™ MO CPU, 256 KB flash memory, and 8 KB RAM memory. Power to the RF beacon 180 was provided by a CR2032 3-volt lithium cell positioned on the underside of the circuit board. The RF beacon 180 device was enclosed in a two-part white plastic disc assembly whose two halves were press-fit and sealed with a Buna-N O-ring so as to be impervious to 1 m immersion in water, such as shown in FIGS. 6B and 6C. The finished device was provisioned as a token or fob to be worn or carried by target patients. A BLE-enabled clinician user app (e.g., an application 143 operating on a mobile device 120) was implemented on iOS 9.3.5 on an iPhone® smartphone device. In this example, a corresponding patient app was also implemented on iOS 9.3.5 on an iPhone® smartphone device. The patients in this example had a major depressive disorder (MDD) and were receiving care in an employer-sponsored clinic. They were provided with the RF beacon 180 disc tokens and downloaded the iOS patient app to their BLE-enabled iPhone® and enabled location services for the app. Each patient received a once-daily message related to their depression management when triggered by their proximity (the proximity of their iPhone®) to the RF beacon 180.

Individual family physicians, psychologists, nurse, dietician, chiropractor, health coach, and social worker clinicians responsible for the care of these patients downloaded the corresponding iOS provider app to their BLE-enabled iPhone® or iPad3® mobile device. UUID was generated so as to refer to the employer's occupational health clinic. Individual patients were identified by a reference pointer comprising a Major number code. A 16-bit Minor number code was segmented, with the first 8 bits divided into two 4-bit segments used to identify two top [active] health condition or problem list categories and the remaining 8 bits further divided into two 4-bit segments, each optionally identifying membership in up to two treatment groups. When one of the beacon-bearing depression patients was in a clinic exam room and one of the participating providers was within range of the patient's beacon, authentication and confirmation of access-authorization for the provider was performed, provider role-associated conditions were retrieved and compared against the conditions identified by the beacon's leading 8 bits' Minor number segments. If the provider's role was related to depression management, then selected depression context-related EHR information pertaining to the individual patient retrieved from a Cerner Millennium EHR was made available on the clinician's mobile device 120, including the EHR-retrieved history of the patient's attendance or 'no-shows' at previous depression management-related appointments. The latter 'no-show' information is strongly correlated with severity or worsening of the patient's depression. If the provider's role was not related to depression management, general medical and nutritional care EHR information pertaining to the individual patient was made available.

Example 2

Multi-beacon group therapy context. In a second example reduction to practice, the hardware and app configuration for multi-beacon usage was the same as Example 1, described above. However, the clinician app (application 143) determined whether a minimum quorum of 2 depression management group members bearing RF beacons 180 were simultaneously in proximity and, if so, group therapy identification was made by quorum being met. If the provider's role was related to delivering group therapy for depression management, then selected group-treatment depression context-related EHR information pertaining to the group was made available on the clinician's mobile device. Otherwise, general medical and nutritional care EHR information pertaining to the group was made available. Since billing and outcomes measurement and provider workload attribution and other aspects differ for group therapy versus individual therapy, the app accomplishes the correct posting of such transactional data to the EHR system regarding the services rendered, in addition to timely provisioning of group therapy-related information at the time of care delivery.

Many different arrangements of the various components depicted, as well as components not shown, are possible without departing from the spirit and scope of the present invention. Embodiments of the present invention have been described with the intent to be illustrative rather than restrictive. Alternative embodiments will become apparent to those skilled in the art that do not depart from its scope. A skilled artisan may develop alternative means of implementing the aforementioned improvements without departing from the scope of the present invention.

It will be understood that certain features and subcombinations are of utility and may be employed without reference to other features and subcombinations and are contemplated within the scope of the claims. Not all steps listed in the various figures need be carried out in the specific order described. Accordingly, the scope of the invention is intended to be limited only by the following claims.

What is claimed is:

1. A system for providing proximity-based mobile-device updates of electronic health records comprising:
    an RF beacon configured to communicate wirelessly information including a reference pointer associated with a target;
    a computer device configured to detect the RF beacon and receive the information including the reference pointer;
    one or more processors; and
    computer storage memory having computer-executable instructions stored thereon which, when executed by the one or more processors, implement a method comprising:
    receiving, by the computer device, information including the reference pointer communicated from the RF beacon;
    using the reference pointer, determining a set of information items associated with the target and of ongoing relevance in making clinical decisions;
    receiving, by the computing device, a subset of information items from the set of information items associated with the target; and
    displaying, on the computer device, at least a portion of the received subset of information to aid a caregiver in making a clinical decision.

2. The system of claim 1, wherein the target comprises a human patient.

3. The system of claim 1, wherein the target comprises a patient monitor device.

4. The system of claim 1, wherein the computing device includes a user interface, the method further comprising receiving via the user interface an indication of one or more information items associated with the target, wherein the determined set of information items associated with the target is related to the one or more information items.

5. The system of claim 1, wherein the RF beacon comprises a BLE-type beacon and wherein the computing device comprises a mobile computing device configured for BLE communication.

6. The system of claim 1, wherein the reference pointer is encoded in a wireless communication emitted by the RF beacon.

7. The system of claim 1, the method further comprising:
detecting, by the computing device, a communication broadcasted by the RF beacon;
in response to detecting the communication, using the broadcasted communication to determine the reference pointer.

8. The system of claim 1, wherein determining the set of information items further includes determining a priority of the information items based on one or more criteria, and wherein the subset of information items includes a portion of the information items having a higher priority.

9. The system of claim 8, wherein the criteria for determining the priority are based on proximity of the computing device to the RF beacon and one or more of: caregiver preferences, caregiver history information, staleness of the information item, condition of the target, the computer device, or a significance-value associated with an information item.

10. A computing device comprising a computer memory and a computer processor that is configured to allow a decision support application to receive proximity-based updates of electronic health records, the computing device comprising:
a communications component configured for wireless communications;
a user interface; and
the decision support application that is a computer program stored on the computer memory having computer instructions that when executed by the computer processor cause the decision support application to:
detect, using the communications component, a communication emitted by an RF beacon, the communication including information encoded in a reference pointer associated with a target;
using the reference pointer, request information for the target;
in response to the request, receive a subset of information items from a set of information items associated with the target, the set of information items determined based on the request; and
display, using the user interface, at least a portion of the received subset of information to aid a caregiver in making a clinical decision.

11. The device of claim 10, wherein the decision support application is further caused to:
receive, from the user, an indication of one or more information items associated with the target, wherein the set of information items is related to the indication received from the user.

12. The device of claim 11, wherein the received indication of one or more information items comprises a subscription to information about the target, wherein the decision support application receives an updated subset of information items until the subscription expires, and wherein the subscription expires after the communication emitted by an RF beacon is no longer detected by the communications component.

13. One or more computer hardware devices having computer-executable instructions embodied thereon that when executed, facilitate a method of providing clinical decision support, the method comprising:
receiving, from a computing device of a patient of a user-caregiver, an indication of one or more information items associated with the that are of ongoing relevance to the user-caregiver in making clinical decisions with respect to the patient;
based on the received indication, determining a set of information items related to the one or more indicated information items;
associating the patient with a designated beacon device implementing a RF protocol for proximity-based communications;
generating a reference pointer associated with the determined set of related information items;
communicating the reference pointer from the beacon device to a mobile device associated with the user-caregiver to enable the user-caregiver to receive updates to the set of related information items on the mobile device, wherein the mobile device is independent of the computing device;
receiving from the mobile device a request for information from the set of information items identified by the reference pointer; and providing, to the mobile device, information from a subset of the determined set of related information items.

14. The one or more computer hardware devices of claim 13, wherein the RF protocol comprises Bluetooth Low Energy (BLE).

15. The one or more computer hardware devices of claim 13, wherein the providing, to the mobile device, information from a subset of the determined set of related information items is in response to determining that at least one of the related information items has been updated.

16. The one or more computer hardware devices of claim 13, wherein determining a set of information items further includes determining a priority of the information items based on one or more criteria, and wherein the subset of information items includes a portion of the information items having a higher priority.

17. The one or more computer hardware devices of claim 16, wherein the criteria for determining the priority are based on proximity of the computing device to the RF beacon and one or more of: caregiver preferences, caregiver history information, staleness of the information item, condition of the target, the computer device, or a significance-value associated with an information item.

18. The one or more computer hardware devices of claim 13, wherein the reference pointer is encoded within a BLE beacon as a UUID, Major number and Minor number codes, and, optionally, associated tag attribute codes stored within the beacon device's flash memory.

19. The one or more computer hardware devices of claim 18, wherein an organization and service are encoded in the UUID, a patient identifier is encrypted in the 16-bit Major number, and one or more related context identifiers are encrypted in the 16-bit Minor number stored on the beacon device.

20. The one or more computer hardware devices of claim 18, wherein an organization and service are encoded in the UUID, a patient identifier is encrypted in the 32-bit segmented key comprised of the Major number and Minor number codes stored on the beacon device, and one or more related context identifiers are encrypted on local flash memory on the beacon device.

* * * * *